United States Patent [19]

Schwab et al.

[11] Patent Number: 5,814,627
[45] Date of Patent: Sep. 29, 1998

[54] 3, 5-DISUBSTITUTED AND 3, 4, 5-TRISUBSTITUTED 2-ISOXAZOLINES AND ISOXAZOLES, PROCESS FOR THEIR PREPARATION AND THEIR USE AS PHARMACEUTICALS

[75] Inventors: Wilfried Schwab; Hiristo Anagnostopulos, both of Wiesbaden; Robert Ryder Bartlett, Darmstadt; Rudolf Schleyerbach; Klaus Ulrich Weithmann, both of Hofheim, all of Germany

[73] Assignee: Hoechst Aktienegesellschaft, Frankfurt am Main, Germany

[21] Appl. No.: 704,743

[22] PCT Filed: Mar. 3, 1995

[86] PCT No.: PCT/EP95/00784

§ 371 Date: Nov. 19, 1996

§ 102(e) Date: Nov. 19, 1996

[87] PCT Pub. No.: WO95/24397

PCT Pub. Date: Sep. 14, 1995

[30] Foreign Application Priority Data

Mar. 10, 1994 [DE] Germany ............... 44 08 084.0

[51] Int. Cl.⁶ ............... A61K 31/42; A61K 31/535; C07D 261/04; C07D 413/12
[52] U.S. Cl. ............... 514/236.8; 514/378; 544/137; 544/367; 546/272.1; 548/6; 548/111; 548/119; 548/205; 548/240; 548/247; 548/248
[58] Field of Search ............... 544/137; 548/240, 548/247; 514/236.8

[56] References Cited

U.S. PATENT DOCUMENTS

| 5,086,064 | 2/1992 | Belliotti et al. . |
| 5,208,251 | 5/1993 | Capiris et al. . |
| 5,510,361 | 4/1996 | Scherz et al. ............... 548/240 |

FOREIGN PATENT DOCUMENTS

| 0245825 | 11/1987 | European Pat. Off. . |
| 0449223 | 10/1991 | European Pat. Off. . |

OTHER PUBLICATIONS

Yasuo Isomura et al., *Chemical and Pharmaceutical Bulletin*, vol. 32,. 1, 1884 Tokyo JP pp. 152–165.

*Chemical Abstracts* vol. 100, No.5 Jan. 30, 1984, abst. #34538 JP A 58 148 858.

Flynn, Daniel L. et al., *Journal of Medicinal Chemistry*, vol. 34, No. 2 (Feb. 1991) pp. 518–521.

*Primary Examiner*—Robert W. Ramsuen
*Attorney, Agent, or Firm*—Finnegan, Henderson, Farabow, Garrett & Dunner, L.L.P.

[57] ABSTRACT

A compound having the formula (I), a physiologically tolerable salt of the compound having the formula (I) and/or a steroisomeric form of the compound having the formula (I), in which one residue $R^1$ or $R^2$ stands for the formula (II), are suitable for preparing medicaments for the therapy of inflammations, asthma, rheumatoid diseases and autoimmune diseases.

12 Claims, No Drawings

3, 5-DISUBSTITUTED AND 3, 4, 5-TRISUBSTITUTED 2-ISOXAZOLINES AND ISOXAZOLES, PROCESS FOR THEIR PREPARATION AND THEIR USE AS PHARMACEUTICALS

This application is a 371 of PCT/E95/00784 filed Mar. 3, 1995.

The present invention relates to pharmaceuticals for the prophylaxis and/or treatment of inflammations, asthma, rheumatic diseases and autoimmune diseases.

The mode of action of non-steroidal anti-inflammatory pharmaceuticals, e.g. acetylsalicylic acid and indomethacin, is already known. It is based on inhibition of the enzyme cyclooxygenase, an enzyme which is present in many cells and which is responsible for providing inflammation-promoting prostaglandins.

It is also already known that cyclooxygenase inhibitors of this type can be employed in rheumatism therapy (EP 245 825).

However, it has meanwhile become clear that, in addition to their undesirable effects, prostaglandins are also able to exert desirable cell-protective properties, for example in thrombocytes, in the gastroduodenum and in the kidney. For this reason, all cyclooxygenase inhibitors bring about undesirable side effects, such as prolongation of the bleeding time, generation of gastric ulcers and inhibition of renal function.

It can, consequently, be of advantage, instead of inhibiting the prostaglandins, to inhibit the particularly potent inflammation-mediators from the substance classes of the leukotrienes and the cytokines, such as interleukin 1 alpha and interleukin 1 beta, oxygen radicals and proteases, by blockading their formation.

It has now been found that while the compound of the formula I essentially exhibits no inhibitory effect on cyclooxygenase, it inhibits the formation of leukotriene, cytokines, oxygen radicals and proteases from white blood cells, and also demonstrates a positive effect in models for testing asthma, autoimmune diseases and rheumatic diseases.

The invention relates to a compound of the formula I

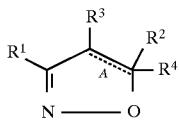

and/or to a physiologically tolerated salt of the compound of the formula I
and/or to a stereoisomeric form of the compound of the formula I;
in this context, one radical $R^1$ or $R^2$ has the meaning of the formula II

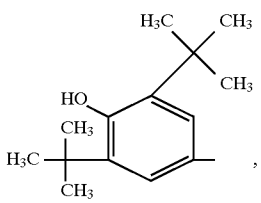

and the other radical $R^1$ or $R^2$ has the following meaning:
a) pyridyl,
b) thiophenyl,
c) thiazolyl,
d) a radical of the formula III

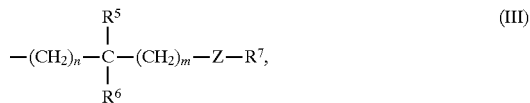

where n is the number zero, 1, 2, 3, 4, 5 or 6, m is the number zero, 1, 2, 3 or 4, Z is
1) —O—, or
2) —NH—, $R^5$ and $R^6$ are, independently of each other,
1) a hydrogen atom,
2) $(C_1-C_4)$-alkyl,
3) $(C_2-C_4)$-alkenyl,
4) $(C_2-C_4)$-alkynyl,
5) phenyl, or
6) OH, and $R^7$ is
1) a hydrogen atom,
2) residue of an amino acid,
3) trifluoromethylsulfonyl,
4) —O—P(O) (OH)$_2$,
5) —O—P(O) (OH)$_2$ mono- or diesterified with phenyl or $(C_1-C_6)$-alkyl, or
6) a radical of the formula IV

in which o is the number zero or 1, and in which $R^9$ and $R^{10}$, independently of each other, have the following meaning:
1) a hydrogen atom, or
2) $(C_1-C_4)$-alkyl, and $R^{11}$ is
1) OH,
2) —O—$(C_1-C_4)$-alkyl,
3) $(C_1-C_{20})$-alkyl,
4) $(C_1-C_{20})$-alkyl, substituted once or more than once, independently of each other, by
4.1 —COOH,
4.2 —OH,
4.3 O-acetyl, or
4.4 =O,
5) —COOH,
6)

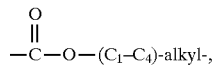

7) N-glycyl,
8) N-glycyl-$(C_1-C_4)$-alkyl ester,
9) N-$(C_1-C_4)$-alkylhydroxylamino,
10) N-(1H-tetrazol-5-yl)amino,
11) 5-methylisoxazol-4-yl,
12) 1-cyano-2-hydroxy-1-propenyl, 13) phenyl,
14) phenyl, substituted once or more than once by 14.1 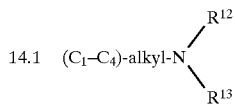

in which $R^{12}$ and $R^{13}$, independently of each other, have the following meaning:
1) a hydrogen atom,
2) $(C_1–C_4)$-alkyl,
3) phenyl-$(C_1–C_2)$-alkyl,
4) $R^{12}$ and $R^{13}$ form, together with the nitrogen atom linking them, a five- to seven-membered heterocycle which is unsubstituted or substituted once to three times by $(C_1–C_4)$-alkyl, it being possible for a carbon atom to be replaced by a sulfur, oxygen or nitrogen atom, or
5) residue of an amino acid, or $R^6$ and $R^7$ are bonded to each other and are, together, from 1 to 3 $CH_2$ radicals, e) a radical of the formula V

in which $Q_1$ is
1) —$(CH_2)_m$—, where n is the number zero, 1, 2, 3 or 4, or
2) —CH=CH—, and $R^8$ is
1) a hydrogen atom,
2) $(C_1–C_4)$-alkyl,
3) OH,
4) —O—$(C_1–C_4)$-alkyl,
5) $NH_2$,
6) N-(1H-tetrazol-5-yl)amino, or
7) N-(3,5-dimethyl-4-hydroxybenzyl)amino, or f) a radical of the formula VI

in which $Q_2$ is
1) —$(CH_2)_m$, where m is the number zero, 1, 2, 3 or 4, or
2) —CH=CH—, and X and Y are, independently of each other,
1) $(C_1–C_4)$-alkyl,
2) —O—$(C_1–C_4)$-alkyl, or
3) OH, ...A... is a double bond which is present or absent, with the restriction that the double bond and the radical $R^4$ are not present simultaneously, $R^4$ is
1) a hydrogen atom, or
2) $(C_1–C_6)$-alkyl, or $R^2$ and $R^4$ form, together with the carbon atom to which they are bonded, an aliphatic ring which is composed of 3, 4 or 5 carbon atoms, and $R^3$ is
1) a hydrogen atom,
2) $(C_1–C_4)$-alkyl, or
3) hydroxy-$(C_1–C_4)$-alkyl.

The compounds of the formula I may be present in the pharmaceuticals as optical isomers, diastereomers or racemates, or as mixtures thereof. The designated alkyl or alkanoyl radicals may be present in either the straight-chain or branched form.

For the purposes of the present invention, five- to seven-membered heterocycles are, for example, pyrrole, pyridine, azepine, thiazole, isothiazole, oxazole, isoxazole, pyrazole, imidazole, thiazine, 1,2-oxazine, 1,3-oxazine, morpholine, pyridazine, pyrimidine, pyrazine, 1,2-thiazepine, 1,3-thiazepine, 1,4-thiazepine, 1,2-oxazepine, 1,3-oxazepine, 1,4-oxazepine, 1,2-diazepine, 1,3-diazepine, 1,4-diazepine and partially or completely saturated variants thereof. Particular mention may be made of pyrrolidine, piperidine, morpholine, piperazine, N-methylpiperazine or pyridine.

The term "an amino acid" is understood to mean the stereoisomeric forms, e.g. D and L forms, of the following compounds:

asparagine, valine, arginine, aspartic acid, glutamine, glutamic acid, tryptophan, β-alanine, lysine, proline, glycine, γ-aminobutyrate, Nε-acetyllysine, Nδ-acetylornithine, Nγ-acetyldiaminobutyrate, Nα-acetyldiaminobutyrate, histidine, isoleucine, leucine, methionine, phenylalanine, serine, cysteine, threonine, alanine and tyrosine. L-Amino acids are preferred. Amino acid residues are derived from the corresponding amino acids. The names of the amino acids are abbreviated in the customary manner. The amino acid residue is bonded to the residue —NH— by means of an amide bond or bonded to the residue —O— via an ester bond.

The following amino acid residues are preferred:
Gly, Ala, Phe, Ser, Thr, Val, β-Ala, γ-aminobutyrate, Asp, Glu, Asn, Gln, Nε-acetyllysine, NΔ-acetylornithine, Nγ-acetyldiaminobutyrate, Nα-acetyldiaminobutyrate, Lys or Tyr.

Preference is given to a compound of the formula I and/or a physiologically tolerated salt of the compound of the formula I and/or a stereoisomeric form of the compound of the formula I, where one radical $R^1$ or $R^2$ has the meaning of the formula II and the other radical $R^1$ or $R^2$ has the following meaning:
a) 2-pyridyl,
b) 4-pyridyl,
c) thiophen-3-yl,
d) 2-thiazolyl,
e) a radical of the formula III, in which n is the number zero, 1, 2, 3 or 4, and m is the number zero or 1, Z is
1) —O—, or
2) —NH—, or $R^5$ and $R^6$ are, independently of each other,
1) a hydrogen atom,
2) $(C_1–C_2)$-alkyl,
3) phenyl, or
4) OH, or $R^6$ and $R^7$ are bonded to each other and together form a methylene group, or $R^7$ is
1) a hydrogen atom,
2) trifluoromethylsulfonyl, 3) an amino acid from the group Gly, Phe, Ala, Lys, Tyr or Ser, or
4) a radical of the formula IV, in which o is the number zero or 1, $R^9$ and $R^{10}$ are, independently of each other,
   1) a hydrogen atom, or
   2) methyl, $R^{11}$ is:
1) OH,
2) —O—$(C_1-C_4)$-alkyl,
3) $(C_1-C_{18})$-alkyl,
4) $(C_1-C_6)$-alkyl, substituted once or more than once, independently of each other, by
   4.1 —COOH,
   4.2 OH, or
   4.3 O-acetyl,
5) —COOH,
6)

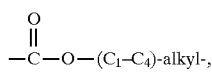
—C—O—$(C_1-C_4)$-alkyl-,

7) N-glycyl,
8) N-glycyl-$(C_1-C_4)$-alkyl ester,
9) N-methylhydroxylamino,
10) N-(1H-tetrazol-5-ylamino),
11) 5-methylisoxazol-4-yl,
12) 1-cyano-2-hydroxy-1-propenyl, or
13) phenyl, substituted once by
    13.1 4-(4-morpholino)-methyl, f) a radical of the formula V, in which $Q_1$ is
   1) —$(CH_2)_m$—, where m is the number zero, 1 or 2, or
   2) —CH=CH—, and $R^8$ is
1) a hydrogen atom,
2) methyl,
3) OH,
4) —O—$(C_1-C_2)$-alkyl,
5) amino,
6) N-(1H-tetrazol-5-yl)amino, or
7) N-3,5-dimethyl-4-hydroxybenzyl, or g) a radical of the formula VI, in which $Q_2$ is
   1) —$(CH_2)_m$—, where m is the number zero, 1 or 2, or
   2) —CH=CH—, X and Y are, independently of each other,
1) methyl,
2) —O—$(C_1-C_2)$-alkyl, or
3) OH, ...A... is a double bond which is present or absent, with the restriction that the double bond and the radical $R^4$ are not present simultaneously, $R^4$ is
1) a hydrogen atom, or
2) $(C_1-C_2)$-alkyl, or $R^2$ and $R^4$ form, together with the carbon atom to which they are bonded, an aliphatic ring having 3, 4 or 5 carbon atoms, $R^3$ is
1) a hydrogen atom,
2) methyl, or
3) hydroxymethyl.

Particular preference is given to a compound of the formula I and/or a physiologically tolerated salt of the compound of the formula I and/or a stereoisomeric form of the compound of the formula I, where one radical $R^1$ or $R^2$ has the meaning of the formula II and the other radical $R^1$ or $R^2$ has the following meaning:
a) 2-pyridyl,
b) 4-pyridyl,
c) thiophen-3-yl,
d) 2-thiazolyl,
e) a radical of the formula III, in which n is the number zero, 1, 2, 3 or 4, and m is the number zero or 1, Z is
1) —O—, or
2) —NH—, or $R^5$ and $R^6$ are, independently of each other,
1) a hydrogen atom,
2) $(C_1-C_2)$-alkyl, or
3) phenyl, or $R^6$ and $R^7$ are bonded to each other and are together a methylene group, or $R^7$ is
1) hydrogen,
2) trifluoromethylsulfonyl,
3) an amino acid from the group Gly, Lys or Phe, or
4) a radical of the formula IV, in which o is the number zero or 1, $R^9$ and $R^{10}$ are, independently of each other,
   1) a hydrogen atom, or
   2) methyl, $R^{11}$ is
1) OH,
2) O-methyl or O-ethyl,
3) $(C_1-C_{18})$-alkyl,
4) $(C_1-C_6)$-alkyl, substituted once or more than once, independently of each other, by
   4.1 —COOH,
   4.2 OH, or
   4.3 O-acetyl,
5) —COOH,
6)

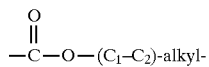
—C—O—$(C_1-C_2)$-alkyl-

7) N-glycyl,
8) N-glycyl-$(C_1-C_2)$-alkyl ester,
9) N-methylhydroxylamino,
10) N-(1H-tetrazol-5-ylamino),
11) 5-methylisoxazol-4-yl, or
12) 1-cyano-2-hydroxy-1-propenyl, f) a radical of the formula V, in which $Q_1$ is
   1) —$(CH_2)_m$—, where m is the number 0, 1 or 2, or
   2) —CH=CH—, and $R^8$ is
1) a hydrogen atom,
2) methyl,
3) OH,
4) —O-methyl,
5) amino,
6) N-(1H-tetrazol-5-yl)amino, or
7) N-3,5-dimethyl-4-hydroxybenzyl, or g) a radical of the formula VI, in which $Q_2$ is
   1) —$(CH_2)_m$—, where m is the number zero or 2, or
   2) —CH=CH—, X and Y are, independently of each other,
1) methyl,
2) —O—($C_1$–$C_2$)-alkyl, or
3) OH, ...A... is a double bond which is present or absent, with the restriction that the double bond and the radical $R^4$ are not present simultaneously, $R^4$ is
1) a hydrogen atom, or
2) methyl, or $R^2$ and $R^4$ form, together with the carbon atom to which they are bonded, an aliphatic ring having 3, 4 or 5 carbon atoms, $R^3$ is
1) a hydrogen atom, or
2) hydroxymethyl.

The compounds listed with structural formulae in Table 1 are very particularly preferred.

The invention also relates to a process for preparing 2-isoxazoline or isoxazole of the formula I and/or a stereoisomeric form of the compound of the formula I and/or a physiologically tolerated salt of the compound of the formula I, wherein a) a primary nitro compound is converted into the corresponding nitrile oxide using isocyanates and catalytic quantities of triethylamine, or a hydroxamoyl chloride, obtained by chlorinating a corresponding aldoxime, is converted into the corresponding nitrile oxide using an organic or inorganic base, and this nitrile oxide, obtained as an intermediate, is reacted, without purification, with an appropriately substituted olefin or alkyne, in the sense of a 1,3-dipolar cycloaddition, to form a 2-isoxazoline or isoxazole of the formula I, and the resulting product is, where appropriate, purified by crystallization or chromatography, or b) a carboxylic ester of the formula I, prepared in accordance with a) or o), or an ester group, additionally introduced via process h) or k), is hydrolyzed to the carboxylic acid, or c) an alkyl carboxylate of the formula I, prepared in accordance with process a) or o), is converted, using an appropriately substituted primary or secondary amine, into the corresponding amide, or d) a monoalkyl phosphinate or dialkyl phosphonate of the formula I, prepared in accordance with a) or o), is hydrolyzed to the phosphonic semi-ester, to the phosphonic acid or to the phosphinic acid, or e) a carboxylic acid, obtained in accordance with b), is initially converted into an activated acid derivative and this derivative is subsequently esterified with alcohols or converted, using primary and secondary amines, into the corresponding amide, or converted, using N-alkylated hyroxylamine, into the corresponding hydroxylamide, or f) N-protective group or O-protective group in a [lacuna] obtained or entrained as an intermediate in accordance with the processes a), b), h), e), o) or g) is eliminated, or carboxylic, phosphinic, phosphonic or phosphoric esters which are introduced or entrained are correspondingly hydrolyzed, and a compound of the formula I is obtained, or g) a compound obtained in accordance with processes f) or o), and having a free amino group, is converted into the corresponding urea derivative by reaction with isocyanate, or converted into the corresponding amide by reaction with an activated carboxylic acid derivative or an N-protected amino acid, or converted into the corresponding sulfonamide by reaction with a sulfonyl chloride, or h) a compound obtained in accordance with processes a), o) or f), and having a free alcohol group, is converted into the corresponding urethane by reaction with isocyanate, or converted into the corresponding ester by reaction with a carboxylic acid derivative which is activated at the carboxyl group and may carry further functional groups, or a corresponding N-protected amino acid derivative, or converted into the corresponding 3-oxobutyrate with diketene, or converted into the corresponding ether by reaction with a halogen compound such as α-halogen-carboxylic acid, or i) a compound obtained in accordance with processes a), o) or f), and having a primary or secondary alcohol group, is oxidized to the corresponding aldehyde or ketone, or k) a carbonyl compound prepared in accordance with process i) is converted into the corresponding crotonic acid derivative by reaction with a base and dialkylphosphonoacetic acid ester, or converted into the corresponding trans-2-(dialkoxyphosphono)vinyl derivative by reaction with tetraalkylmethylenediphosphonate, or l) an epoxide group introduced during the cycloaddition is converted into the corresponding 1,2-diol, or m) an amide prepared in accordance with process g), and containing a 3-H-isoxazole ring, is converted into the corresponding substituted 2-cyano-3-hydroxycrotonamide by treatment with a base in the sense of a ring opening, or n) a compound of the formula I prepared in accordance with processes a)–m), which compound, owing to its chemical structure, occurs in enantiomeric forms, is resolved into the pure enantiomers by salt formation with enantiomerically pure acids or bases, chromatography on chiral stationary phases, or derivatization using chiral enantiomerically pure compounds such as amino acids, separation of the diastereomers thus obtained, and elimination of the chiral auxiliary group, or o) a mixture of 2-isoxazoline diastereomers of the formula I, obtained by cycloaddition to chiral or racemic olefins, is resolved into the pure diastereomers by column chromatography on silica gel, or p) the compound of the formula I prepared in accordance with processes a)–o) is either isolated in free form or, where acid or basic groups are present, is, where appropriate, converted into physiologically tolerated salts, or q) a compound prepared in accordance with process h), which compound carries a further functional group such as a halomethyl group, is alkylated with a primary or secondary amino group or etherified with an alcohol.

The preparation of physiologically tolerated salts from compounds of the formula I, including their stereoisomeric forms, which are capable of salt formation is effected in a manner known per se. The carboxylic acids, phosphonic acids and phosphinic acids, and also the phosphonic acid semi-esters, form stable alkali metal salts, alkaline earth metal salts or optionally substituted ammonium salts with basic reagents such as hydroxides, carbonates, hydrogen carbonates or alcoholates, and also ammonia or organic bases, for example trimethylamine, amine, triethylamine or ethanolamine, and also basic amino acids, for example lysine, ornithine or arginine. Inasfar as the compounds of the formula I possess basic groups in the $R^1$ or $R^2$ radical, stable acid addition salts can also be prepared using strong acids. Both inorganic and organic acids, such as hydrochloric acid, hydrobromic acid, sulfuric acid, phosphoric acid, methanesulfonic acid, benzenesulfonic acid, p-toluenesulfonic acid, 4-bromobenzenesulfonic acid, cyclohexylamidosulfonic acid, trifluoromethylsulfonic acid, acetic acid, oxalic acid, tartaric acid or trifluoroacetic acid are suitable for this purpose.

The preparation and conversion of the nitrile oxides used as starting compounds for 1,3-dipolar cycloadditions is described in a recent monograph (K. P. G. Torsell: Nitrile Oxides, Nitrones and Nitronates in Organic Synthesis, VCH Verlagsgesellschaft, Weinheim, 1988). The hydroxamoyl halides serving as precursors may be obtained, in accordance with processes known from the literature, by halogenating corresponding aldoximes or, in the case of chloroxyiminoacetic esters, via a diazotization reaction proceeding from alkyl esters of glycine (G. S. Skinner, J. Am. Chem. Soc. 64 (1924), 731). If tert-butyl hypochlorite is used for chlorinating the aldoximes, there is no need to isolate the corresponding hydroxamoyl chlorides. The nitro compounds which are also used are in some cases known from the literature, or can be prepared by methods which are in principle known from the literature, thus, for example, 4-nitrobutyric esters by the fluoride-catalyzed or base-catalyzed addition of nitromethane to acrylic acid derivatives (D. W. Chasar, Synthesis 1982, 841–42; N. Ono, Synthesis 1984, 226–227).

The yields which are known from the literature can be substantially improved, and the formation of bis-adducts, which normally appear as by-products which are difficult to separate off, to a very large extent prevented, by conducting the reaction in a special way and using 1,8-diazabicyclo [5.4.0]undec-7-ene (DBU) as the base.

The optionally substituted alkene or alkyne derivatives which also serve as reactants are, as parent substances, for the most part known from the literature or can even be obtained commercially. Appropriate directions are given in the examples. Production of the nitrile oxides, which easily tend to oligomerization, advantageously takes place "in situ" in the presence of the olefinic or acetylenic reactant without any intermediate isolation. When they are produced from nitro compounds in accordance with the method of Mukaiyama, aromatic isocyanates, for example phenyl isocyanate or diisocyanatobenzene, are preferably employed for the dehydration. In this case, it is advisable to carry out the reaction in an aprotic solvent or partitioning agent which is inert towards the reactants, such as ethyl acetate, dimethylformamide, dimethylacetamide, dialkyl ether, tetrahydrofuran, halogenated hydrocarbons, e.g. dichloromethane, chloroform or dichloroethane, hydrocarbons, such as hexane, cyclohexane, benzene, toluene or other substituted aromatic compounds, with mixtures of the abovementioned solvents also being suitable. Organic or inorganic bases, such as tertiary amines, alkali metal carbonates or alkali metal hydroxides, are used for producing the nitrile oxides from hydroxamoyl halides. In this case, when organic bases are used, the reaction is preferably carried out in the abovementioned, optionally chlorinated, aliphatic or aromatic hydrocarbons or aliphatic, and also cyclic, ethers, whereas, when inorganic bases are used, the reaction can additionally also be carried out in two-phase solvent mixtures, for example ethyl acetate/water or dichloromethane/water. The preparation of the nitrile oxides and the cycloaddition are as a rule effected at temperatures of from −20° C. to +80° C., preferably, however, of from 0° to +40° C.

The hydrolysis of the alkyl esters which are entrained in the cycloaddition, or introduced subsequently by way of further reactions, to the corresponding carboxylic acids is as a rule achieved using aqueous alkali, which can be employed in equimolar quantity or in excess, in aqueous solution, or, if the starting compound is poorly soluble in water, in aqueous/organic solvent mixtures, with water/alcohol mixtures having proved to be of particular value.

The cleavage of the amine, alcohol or carboxylic acid protective groups entrained in the substituents $R^1$ or $R^2$ of the general formula I is usually effected in accordance with methods known from peptide chemistry, an acidic elimination, for example using alcoholic hydrochloric acid or trifluoroacetic acid, being preferred in the case of the tert-butoxycarbonyl group, which is preferably used, whereas lower alkyl esters are preferably cleaved under alkaline conditions.

The conversion of the phosphonic esters and phosphinic esters into the corresponding free acids is achieved under acidic conditions, preferably in a water-free medium, for example by using hydrobromic acid in organic acids such as acetic acid, or by using trimethylbromosilane or trimethyliodosilane in aprotic solvents, with halogenated hydrocarbons preferably being employed. In this case, a range of from 0° to 50° C. is selected as the reaction temperature to ensure cleavage under mild conditions. The phosphonic semi-esters are as a rule prepared by subjecting the phosphonic diesters to alkaline hydrolysis.

Compounds of the formula I having a free carboxylic acid function in $R^1$ or $R^2$ can, following appropriate activation of the carboxyl group, be converted, in a manner known per se, into the corresponding amides using primary and secondary amines and also using N-alkylated hydroxylamines amines or 5-aminotetrazole.

Compounds of the formula I having a free alcohol or amine function in $R^1$ or $R^2$ can be converted into the corresponding ester or amide derivatives using activated carboxylic acid derivatives such as acid halides or acid anhydrides. Corresponding esters or amides can also be obtained by proceeding from N-protected amino acids. In this case, methods known from peptide chemistry are advantageously employed for activating the amino acid component, for example the hydroxybenzotriazole/ dicyclohexylcarbodiimide method (W. König, R. Geiger, Chem. Ber. 103 (1970), 2034–2040) or activation using propanephosphonic anhydride (PPA), it also being possible to use chlorinated hydrocarbons, such as dimethylformamide, as solvents in addition to aliphatic and cyclic ethers. Tertiary amines, such as triethylamine, N-ethylmorpholine or pyridine, are preferred as auxiliary bases. The reaction is carried out in a temperature range of from −10° C. to +50° C., preferably at from 0° C. to +20° C.

Inasfar as the acyl derivatives which are present in protected form are required in the form of free amino functions or carboxylic acid functions, the corresponding protective groups can be removed either individually or together by the methods which have already been described above.

In addition to this, compounds of the formula I having a free alcohol or amine function in $R^1$ or $R^2$ can be converted into urethane derivatives or urea derivatives by addition to appropriately substituted isocyanates. The ester groups, which are entrained in association with the isocyanate addition or are introduced as an additional function, can, as described above, be converted into the corresponding carboxylic acids.

Compounds having a free primary or secondary alcohol function can be oxidized to the corresponding aldehydes or ketones in a simple manner by the method, known as "Swern oxidation", using dimethyl sulfoxide and oxalyl chloride. In this case, side reactions such as oxidation of the phenol ring or oxidative degradation of the 2-isoxazoline ring can be avoided by appropriate conduct of the reaction at a low temperature. The carbonyl compounds thus obtained can be converted into the correspondingly substituted trans-olefins using bases and CH— acidic compounds, such as alkyl dialkylphosphonoacetates or tetraalkylmethylenediphosphonate, in the sense of a condensation.

Inasfar as the compounds of the formula I occur in diastereoisomeric or enantiomeric forms, and arise as their mixtures in the chosen synthesis, their resolution into the pure stereoisomers is achieved either by means of chromatography on an optionally chiral support material, or, inasfar as the racemic compounds of the formula I are capable of salt formation, by means of fractional crystallization of the diastereomeric salts formed with an optically active base or acid as auxiliary substance. Examples of suitable chiral stationary phases for the resolution, by thin layer chromatography or column chromatography, of enantiomers of the 2-isoxazolines having an asymmetric C atom in the 5-position, which as a rule arise in racemic form, are modified silica gel supports (so-called Pirkle phases) and also high-molecular carbohydrates, for example triacetylcellulose. Following appropriate derivatization, known to the person skilled in the art, gas-chromatographic methods on chiral stationary phases can also be used for analytical purposes. In order to resolve the enantiomers of the racemic carboxylic acids, phosphonic acids and phosphinic acids, the diastereomeric salts, of differing solubility, are formed using an optically active, as a rule commercially available, base, for example (−)-nicotine, (+)- and (−)-phenylethylamine, quinine bases, L-lysine or L- and D-arginine, the more sparingly soluble component is isolated as a solid, the more readily soluble diastereomer is separated off from the mother liquor, and the pure enantiomers are isolated from the diastereomeric salts which have been obtained in this way.

The racemic compounds of the formula I which contain a basic group such as an amino group can, in a manner which is in principle identical, be converted into the pure enantiomers using optically active acids such as (+)-camphor-10-sulfonic acid, D- and L-tartaric acid, D- and L-lactic acid or (+) and (−)-mandelic acid. Chiral compounds which contain alcohol or amine functions can also be converted into the corresponding esters or amides using appropriately activated or optionally N-protected enantiomerically pure amino acids, or, conversely, chiral carboxylic acids can be converted into the amides using carboxyl-protected enantiomerically pure amino acids, or into the corresponding chiral esters using enantiomerically pure hydroxycarboxylic acids such as lactic acid. The chirality of the amino acid residue or alcohol radical introduced in enantiomerically pure form can then be used for resolving the isomers by carrying out a resolution of what are now diastereomers by crystallization or chromatography on suitable stationary phases, and after that once again eliminating the entrained chiral molecule moiety using suitable methods.

The invention also relates to pharmaceuticals which are characterized by an effective content of at least one compound of the formula I and/or a stereoisomeric form of the compound of the formula I and/or a physiologically tolerated salt of the compound of the formula I, in addition to pharmaceutically suitable and physiologically tolerated excipients, additives and/or active compounds and auxiliary substances. The pharmaceuticals according to the invention may be administered intravenously, parenterally, topically, rectally or orally.

The pharmaceuticals according to the invention are suitable, in preference, for the prophylaxis and/or therapy of asthmatic diseases, inflammations and autoimmune diseases.

These include, for example, rheumatic diseases, acute and chronic inflammations of muscles, joints or the gastrointestinal tract, allergic respiratory tract diseases, psoriasis or autoimmune diseases, e.g. systemic lupus erythematodes (SLE), type II diabetes, myasthenia gravis, Sjögren's syndrome, dermatomyositis, sclerodermia or multiple sclerosis (MS).

The invention also relates to a process for preparing a pharmaceutical according to the invention, wherein at least one compound of the formula I is brought into a suitable form for administration together with a pharmaceutically suitable and physiologically tolerated excipient and, where appropriate, further suitable active compounds, additives or auxiliary substances.

Examples of suitable solid or liquid pharmaceutical forms of preparation are granules, powders, coated tablets, tablets, (micro)capsules, suppositories, syrups, juices, suspensions, emulsions, drops or injectable solutions and also preparations having a protracted release of active compound, in the preparation of which forms customary adjuvants, such as carrier substances, disintegrants, binding agents, coating agents, swelling agents, glidants, lubricants, flavorants, sweeteners and solubilizers are employed. Examples of frequently used auxiliary substances which may be mentioned are magnesium carbonate, titanium dioxide, lactose, mannitol and other sugars, talc, milk protein, gelatin, starch, cellulose and its derivatives, animal and vegetable oils, such as cod liver oil, sunflower oil, groundnut oil or sesame oil, polyethylene glycols and solvents, such as, for example, sterile water and monohydric or polyhydric alcohols, for example glycerol.

The pharmaceutical preparations are preferably prepared and administered in dosage units, with each unit containing, as the active constituent, a defined dose of the compound of the formula I according to the invention. In the case of solid dosage units, such as tablets, capsules, coated tablets or suppositories, this dose can be up to about 1000 mg, preferably, however, from about 50 to 300 mg, and, in the case of solutions for injection in ampoule form, up to about 300 mg, preferably, however, from about 10 to 100 mg.

Depending on the activity of the compound of the formula I, both in humans and animals, daily doses of from about 50 to 3000 mg of active compound, preferably from about 150 to 1000 mg, in the case of oral administration, and of from about 50 to 1000 mg, preferably from about 100 to 300 mg, in the case of intravenous administration, are indicated for the treatment of an adult patient of about 70 kg in weight. However, it can sometimes also be appropriate to administer higher or lower daily doses. The daily dose can be administered either on one occasion in the form of a single dosage unit or of several smaller dosage units, or on several occasions in the form of subdivided doses given at defined intervals. Finally, the compounds of the formula I and/or, where appropriate, their physiologically tolerated salts can also be formulated, when preparing the abovementioned pharmaceutical forms of administration, together with other suitable active compounds, for example blood flow-promoting substances, inhibitors of blood platelet aggregation, inhibitors of thrombocyte aggregation, calcium antagonists, antithrombotic agents, anti-hyperlipidemia agents, neuroprotective agents, analgesics, sedatives, antidepressants, anti-inflammatory agents, anti-anginal agents, cardiotonics, antiarrhythmic agents, diuretics, antihypertensive agents, including β-receptor blockers and calcium blockers, plasma expanders and other vasotherapeutic agents.

The structural formulae of the preparation examples described below are assembled, together with the melting points and the $^1$H NMR data, in Table 1. Where stereoisomeric forms are present, the relative configuration is given in the structural formulae. The delta values of the NMR spectra listed below are given in ppm.

EXAMPLE 1

3-(4-Hydroxy-3,5-di-tert-butylphenyl)-5-hydroxymethyl-2-isoxazoline a) 3-(4-Hydroxy-3,5-di-tert-butyl)benzaldoxime The oxime was prepared by processes known from the literature (Houben-Weyl: Meth. d. Org. Chem. (Methods of Organic Chemistry), Vol. X/4, pp. 55 ff), proceeding from 3-(4-hydroxy-3,5-di-tert-butyl)benzaldehyde.

b) 1,3-dipolar cycloaddition with nitrile oxide 24.9 g (0.1 mol) of the aldoxime prepared under a) were dissolved in 250 ml of dichloromethane, 12.0 g (0.11 mol) of tert-butyl hypochlorite were added dropwise, while cooling, and, once the dropwise addition was complete, the mixture was then stirred at room temperature for a further 45 min. After adding 11.6 g (0.2 mol) of allyl alcohol, 16.7 ml (0.12 mol) of triethylamine, dissolved in 150 ml of dichloromethane, were slowly added dropwise (over a period of 6 hours). The mixture was stirred overnight, washed with water, dilute aqueous citric acid, and NaCl solution, dried over sodium sulfate and concentrated under reduced pressure. The product was obtained in crystalline form by crystallization from tert-butyl methyl ether/petroleum ether. Yield: 13.1 g The examples: 2, 5, 8, 9, 10, 11, 12, 13, 14, 15, 16, 17, 18, 19, 20, 21, 22, 23, 24, 25, 26, 27, 28, 29, 30, 31, 32, 35, 44, 48, 66, 67, 68, 69, 78, 79 and 80 described in Table 1 below were prepared in analogy with Example 1 by cycloaddition of the nitrile oxides, prepared in situ, to the corresponding olefins or alkynes.

In the case of crude products which initially arise as oils, chromatography on silica gel, using tert-butyl methyl ether/petroleum ether or ethyl acetate/petroleum ether mixtures, and subsequent crystallization has also proved to be of value.

Peculiarities regarding the synthesis of the examples listed in Table 1:

Regarding Ex. 2)

The synthesis of the olefin structural component is described in EP 0220573.

Regarding Ex. 8)

3-Vinylthiophene: CAS No. 13679-64-6

Regarding Ex. 11)

Cycloaddition to methyl acrylates. Conversion into the amide was effected using saturated methanolic ammonia solution in excess at room temperature.

Regarding Ex. 14)

Cycloaddition to N-(3,5-dimethyl-4-hydroxybenzyl) methacrylamide (synthesis described in DE 3820699).

Regarding Ex. 15)

Owing to the non-stereoselective cycloaddition, the product arises as a diastereomeric mixture.

Regarding Ex. 16 and 17)

The racemic erythro/threo diastereomeric mixture arising in association with the cycloaddition to butadiene monoxide was resolved into the diastereomers by means of chromatography on silica gel using petroleum ether/ethyl acetate 9:1 and subsequent crystallization (Example 16: rac. erythro isomer, Example 17: rac. threo isomer).

Regarding Ex. 18–20)

The racemic erythro/threo diastereomeric mixture (Ex. 18) arising by cycloaddition to 1-buten-3-ol was resolved into the diastereomers by means of chromatography on silica gel using petroleum ether/tert-butyl methyl ether 5:1 (Ex. 19: rac. erythro isomer, Ex. 20: rac. threo isomer).

Regarding Ex. 21–22)

The racemic erythro/threo diastereomeric mixture arising by cycloaddition to 1-buten-3-ol acetate was resolved into the diastereomers by means of chromatography on silica gel using petroleum ether/ethyl acetate 19:1 (Ex. 21: rac. erythro isomer, Ex. 22: rac. threo isomer)

Regarding Ex. 23)

The cycloaddition was carried out using tert-butyl acrylate. The tert-butyl ester group was eliminated using trifluoroacetic acid in dichloromethane at room temperature. After concentrating, it was possible to crystallize the product from tert-butyl methyl ether/petroleum ether.

Regarding Ex. 35)

The synthesis of the olefin structural component is described in EP 0220573.

Regarding Ex. 48)

The cycloaddition was carried out using N-tert-butoxycarbonylpropargylamine. The N-protective group was subsequently eliminated using trifluoroacetic acid. It was possible to obtain the product, in crystalline form as the trifluoroacetate, from methanol/tert-butyl methyl ether. The free base was obtained by extraction from aqueous dilute NaOH using dichloromethane, and drying and concentrating the organic phase.

Regarding Ex. 78)

The cycloaddition was carried out using 6-heptene-2,4-diol. A product, which was isomerically pure by NMR spectroscopy, was obtained by chromatography on silica gel using tert-butyl methyl ether/petroleum ether and subsequent repeated crystallization from the above solvents.

Regarding Examples 79) and 80)

The cycloaddition was carried out in analogy with Example 1) using an excess of 1,6-heptadien-4-ol. Resolution into the diastereoisomers was effected by means of chromatography on silica gel using petroleum ether/ethyl acetate mixtures (gradient 6:1–2:1). It was not possible to classify the threo/erythro isomers by NMR spectroscopy.

EXAMPLE 3

2-(3-(4-Hydroxy-3,5-di-tert-butylphenyl)-2-isoxazolin-5-ylmethoxy)methylpropionic acid 4.0 g (0.0095 mol) of the product from Example 2 were dissolved in 80 ml of methanol, and 25 ml of aqueous 1N NaOH were added; once the hydrolysis was complete (monitoring by TLC), the mixture was acidified with 25 ml of 1N HCl. The precipitated product was filtered, washed with water and dried. Yield: 3.0 g

EXAMPLE 4

N-(3-(4-Hydroxy-3,5-di-tert-butylphenyl)-2-isoxazolin-5-ylmethoxycarbonyl)glycine a) Reaction with isocyanate 5.5 g (0.018 mol) of the product from Example 1 were dissolved in 5 ml of dichloromethane, 3.2 g (0.025 mol) of ethyl isocyanoacetate and approximately 4 drops of triethylamine were added, and the mixture was heated at 50°–60° C. while stirring. Once the reaction was complete (monitoring by TLC), the mixture was concentrated and chromatographed on silica gel using tert-butyl methyl ether/petroleum ether. Yield: 7.2 g of oily product.
b) Hydrolysis of the ethyl ester 7.2 g of the product from a) were, as described in Example 3), hydrolyzed with an excess of 1N NaOH and, after acidification, isolated in crystalline form.

Yield: 4.56 g.

EXAMPLE 6

3-(4-Hydroxy-3,5-di-tert-butylphenyl)-2-isoxazolin-5-ylphosphonic acid 5.0 g (0.013 mol) of the product from Example 5 were treated, at room temperature, with approximately 100 ml of a 33% solution of HBr in glacial acetic acid until the reaction was complete (monitoring by TLC). The residue remaining after concentration was thoroughly stirred with tert-butyl methyl ether. Yield: 3.15 g.

EXAMPLE 7

Monomethyl 3-(4-hydroxy-3,5-di-tert-butylphenyl)-2-isoxazolin-5-ylphosphonate 5.0 g (0.013 mol) of the product from Example 5 were dissolved, at room temperature, in 100 ml of methanol. 30 ml of 1N NaOH were added, and the mixture was stirred for 15 hours (monitoring by TLC). After having been acidified (1N HCl), the mixture was extracted with dichloromethane, followed by washing with water and saturated NaCl solution, drying and concentration. The residue was crystallized from tert-butyl methyl ether/petroleum ether. Yield: 3.4 g.

EXAMPLES 21 AND 22

(alternative synthesis)

1-(3-(4-Hydroxy-3,5-di-tert-butylphenyl)-2-isoxazolin-5-yl)ethyl acetate (erythro or threo isomer, respectively) 2.5 g (0.008 mol) of the product from Examples 19 or 20 were dissolved in 100 ml of dichloromethane and 6 ml of pyridine. After adding 125 mg of 4-dimethylaminopyridine, 1.35 ml (0.024 mol) of acetyl chloride, dissolved in 10 ml of dichloromethane, were added dropwise, while cooling with ice; once the reaction was complete (monitoring by TLC), the mixture was washed with water, aqueous potassium hydrogen sulfate solution and water, dried and concentrated. The remaining oil was crystallized from tert-butyl methyl ether/petroleum ether.

EXAMPLE 33

Ethyl (1-(3-(4-hydroxy-3,5-di-tert-butylphenyl) isoxazol-5-yl)-1-methylethoxy)acetate 10.0 g (0.03 mol) of the product from Example 29, dissolved in 40 ml of absolute dimethylformamide, were added dropwise, under a protective gas and while cooling with ice, to a suspension of 1.06 g (0.044 mol) of sodium hydride in 30 ml of absolute dimethylformamide. After a further 30 min without cooling, 10.8 g (0.044 mol) of ethyl bromoacetate, dissolved in 30 ml of absolute dimethylformamide, were added dropwise and the mixture was then stirred for a further 4 hours. The reaction mixture was then poured onto ice, extracted with ethyl acetate, washed with water, dried and concentrated. The oily residue was crystallized from petroleum ether.

Yield: 6.8 g.

EXAMPLE 34

(1-(3-(4-Hydroxy-3,5-di-tert-butylphenyl)isoxazol-5-yl)-1-methylethoxy)acetic acid 3.7 g (0.009 mol) of the product from Example 33 were hydrolyzed in analogy with Example 3. Yield: 2.9 g.

EXAMPLE 36

2-(3-(4-Hydroxy-3,5-di-tert-butylphenyl)isoxazol-5-ylmethoxy)-2-methylpropionic acid 9.5 g (0.023 mol) of the product from Example 35 were hydrolyzed in analogy with Example 3. Yield: 6.6 g.

EXAMPLE 37

N-Methylhydroxamoyl-2-((3-(4-hydroxy-3,5-di-tert-butylphenyl)isoxazol-5-ylmethoxy)-2-methyl propionate 4.0 g (0.01 mol) of the product from Example 36 were derivatized, in analogy with a method in the literature (EP 0 199 151), using oxalyl chloride and N-methylhydroxylamine. The product was crystallized from tert-butyl methyl ether. Yield: 2.7 g.

EXAMPLE 38

2-(3-(4-Hydroxy-3,5-di-tert-butylphenyl)isoxazol-5-ylmethoxy)-N-(1H-tetrazol-5-yl)isobutyramide 6.0 g (0.015 mol) of the product from Example 36 were derivatized, in analogy with a method in the literature (J Org Chem, 34 (1969), 2766–2767) using 1.7 ml (0.015 mol) of silicon tetrachloride and 1.25 g (0.015 mol) of 5-aminotetrazole in absolute pyridine. The product was crystallized from tert-butyl methyl ether/petroleum ether. Yield: 3.9 g.

EXAMPLE 39

N-(3-(4-Hydroxy-3,5-di-tert-butylphenyl)isoxazol-5-ylmethoxycarbonyl)glycine ethyl ester 14.0 g (0.046 mol) of the product from Example 24 were reacted in analogy with Example 4a). The remaining oil was purified by chromatography on silica gel using tert-butyl methyl ether/petroleum ether 1:4. Yield: 16.4 g.

EXAMPLE 40

N-(3-(4-Hydroxy-3,5-di-tert-butylphenyl)isoxazol-5-ylmethoxycarbonyl)glycine 7.1 g (0.06 mol) of the product from Example 39 were hydrolyzed in analogy with Example 3. Yield: 4.1 g.

EXAMPLE 41

N-(3-(4-Hydroxy-3,5-di-tert-butylphenyl)isoxazol-5-ylpropoxycarbonyl)glycine ethyl ester 8.0 g (0.024 mol) of the product from Example 26 were reacted in analogy with Example 4a). The remaining oil was purified by crystallization from tert-butyl methyl ether/petroleum ether. Yield: 6.1 g.

EXAMPLE 42

N-(3-(4-Hydroxy-3,5-di-tert-butylphenyl)isoxazol-5-ylpropoxycarbonyl)glycine 4.0 g (0.0089 mol) of the product from Example 41 were hydrolyzed in analogy with Example 3. Yield: 2.8 g.

EXAMPLE 43

N-(2-(4-Hydroxy-3,5-di-tert-butylphenyl)isoxazol-5-ylethoxycarbonyl)glycine 6.25 g of the product from Example 25 were reacted in analogy with Example 4a). The remaining product was hydrolyzed in analogy with Example 3 and purified by chromatography on silica gel using tert-butyl methyl ether and finally by crystallization from tert-butyl methyl ether/petroleum ether. Yield: 3.8 g.

EXAMPLE 45

3-(4-Hydroxy-3,5-di-tert-butylphenyl)isoxazol-5-ylpropionic acid 4.3 g (0.011 mol) of the product from Example 44 were hydrolyzed in analogy with Example 3. Yield: 3.0 g.

EXAMPLE 46

3-(3-(4-Hydroxy-3,5-di-tert-butylphenyl)isoxazol-5-yl)-N-(1H-tetrazol-5-yl)propionamide 7.0 g (0.02 mol) of the product from Example 45 were derivatized, in analogy with Example 38, using silicon tetrachloride and 5-aminotetrazole in absolute pyridine. The product was crystallized from tert-butyl methyl ether/petroleum ether. Yield: 6.5 g.

EXAMPLE 47

3-(4-Hydroxy-3,5-di-tert-butylphenyl)isoxazol-5-ylacrylic acid a) Swern oxidation to form the aldehyde 25.4 g (0.2 mol) of oxalyl chloride were initially introduced in 250 ml of absolute dichloromethane, at −60° C. and under a protective gas, and 31.2 ml (0.044 mol) of dimethyl sulfoxide, dissolved in 20 ml of absolute dichloromethane, were then added dropwise. After 30 min, 30.3 g (0.1 mol) of the product from Example 24, dissolved in 200 ml of absolute dichloromethane/20 ml of dimethylformamide, were added dropwise, at −50° C. and within 45 min, and the mixture was subsequently stirred for 20 min. After adding 55.6 ml (0.4 mol) of triethylamine, the cooling was removed and the mixture was subsequently stirred at room temperature for 1 hour, washed with water, dilute aqueous citric acid and NaCl solution, dried and concentrated. The remaining oil was purified by chromatography on silica gel using tert-butyl methyl ether/petroleum ether 1:9, and crystallized from petroleum ether. Yield: 16.4 g.

b) Olefination 0.77 g (0.032 mol) of sodium hydride were initially introduced into 40 ml of absolute tetrahydrofuran, at 0° C. and under a protective gas, 5.05 g (0.024 mol) of methyl diethylphosphonoacetate, dissolved in 50 ml of absolute tetrahydrofuran, were added dropwise, and the resulting suspension was subsequently stirred at 0° C. for 1 hour; 4.8 g (0.016 mol) of the product from Example 47a), dissolved in 50 ml of absolute tetrahydrofuran, were then added dropwise, and the mixture was subsequently stirred for a further 2 hours, poured into ice water, extracted several times with dichloromethane, washed with water, dried and concentrated. The product was crystallized from tert-butyl methyl ether/petroleum ether. Yield: 4.2 g.

c) Hydrolysis 3.7 g (0.01 mol) of the product from Example 47b) were hydrolyzed in analogy with Example 3. Yield: 3.3 g.

EXAMPLE 49

N-(3-(4-Hydroxy-3,5-di-tert-butylphenyl)isoxazol-5-ylmethyl)trifluoromethanesulfonamide 3.6 g (0.012 mol) of the base form of the product from Example 48, dissolved in 50 ml of absolute dichloromethane, were initially introduced, while cooling with ice, and 3.95 g (0.014 mol) of trifluoromethanesulfonic anhydride and, subsequently, 2.2 ml (0.017 mol) of N-ethylmorpholine were added; the mixture was subsequently stirred overnight, washed with water, dilute aqueous citric acid and NaCl solution, dried and concentrated. The remaining oil was purified by chromatography on silica gel using tert-butyl methyl ether/petroleum ether 3:1, and crystallized from tert-butyl methyl ether/petroleum ether. Yield: 2.1 g.

EXAMPLE 50

Ethyl N-(3-(4-hydroxy-3,5-di-tert-butylphenyl)isoxazol-5-ylmethyl)oxalamate 9.1 g (0.03 mol) of the base form of the product from Example 48 were acylated, in absolute tetrahydrofuran and while cooling with ice, with 3.9 ml (0.035 mol) of ethyl (chloroformyl)formate and 9.7 ml (0.07 mol) of triethylamine in analogy with a method in the literature (J Med Chem, 34 (1991), 600). After adding ice water, and extracting with ethyl acetate, washing took place with water, dilute aqueous citric acid and NaCl solution, followed by drying and concentration. The remaining oil was crystallized from tert-butyl methyl ether/petroleum ether. Yield: 9.1 g.

EXAMPLE 51

N-(3-(4-Hydroxy-3,5-di-tert-butylphenyl)isoxazol-5-ylmethyl)oxalamic acid 5.0 g (0.012 mol) of the product from Example 50 were hydrolyzed in analogy with Example 4b). The product, arising as an oil, was isolated by extraction with dichloromethane, washing with water and NaCl solution, drying and concentrating. The remaining amorphous product was crystallized from tert-butyl methyl ether/petroleum ether. Yield: 3.4 g.

EXAMPLE 52

5-Methylisoxazol-4-carboxylic acid(3-(4-hydroxy-3,4-di-tert-butylphenyl)isoxazol-5-ylmethyl)amide 5.0 g (0.0165 mol) of the base form of the product from Example 48 were initially introduced in 80 ml of absolute tetrahydrofuran, while cooling with ice, together with 2.2 ml (0.017 mol) of N-ethylmorpholine, and 2.5 g (0.017 mol) of 5-methylisoxazol-3-ylcarbonyl chloride, dissolved in 10 ml of tetrahydrofuran, were then added dropwise; the mixture was subsequently stirred at room temperature for 5 hours. After adding ice water and extracting with dichloromethane, washing took place with water, dilute aqueous citric acid and NaCl solution, followed by drying and concentration. The oil which was obtained was purified by chromatography on silica gel using tert-butyl methyl ether/petroleum ether 1:1 and crystallized from petroleum ether. Yield: 4.9 g.

EXAMPLE 53

2-Cyano-3-hydroxybut-2-enecarboxylic acid(3-(4-hydroxy-3,5-di-tert-butylphenyl)isoxazol-5-ylmethyl)amide 4.0 g (0.01 mol) of the product from Example 52 were dissolved in 50 ml of absolute tetrahydrofuran, and 20 ml of 1N NaOH were added while cooling with ice; once the reaction was complete (monitoring by TLC), the mixture was acidified with 22 ml of 1N HCl and extracted with dichloromethane; this was followed by washing, drying and concentration. The remaining residue was crystallized from tert-butyl methyl ether/petroleum ether. Yield: 3.3 g.

EXAMPLE 54

Ethyl (3-(3-(4-hydroxy-3,5-di-tert-butylphenyl)isoxazol-5-ylmethyl)ureido) acetate 14.2 g (0.047 mol) of the base form of the product from Example 48 were heated, as the substance itself, at 50°–60° C., while stirring, together with 6.5 g (0.05 mol) of ethyl isocyanoacetate. Once the reaction was complete (monitoring by TLC), the mixture was concentrated and crystallization took place from tert-butyl methyl ether/petroleum ether. Yield: 11.3 g.

EXAMPLE 55

L-Phenylalanyl-N-(3-(4-hydroxy-3,5-di-tert-butylphenyl)-isoxazol-5-ylmethyl)amide hydrochloride a) Acylation using N-tert-butoxycarbonylphenylalanine 5.3 g (0.02 mol) of N-tert-butoxycarbonylphenylalanine were dissolved in 100 ml of anhydrous tetrahydrofuran, 4.5 g (0.022 mol) of dicyclohexylcarbodiimide and 3.1 g (0.02 mol) of 1-hydroxybenzotriazole hydrate were added, and the mixture was stirred for about 45 min. The urea which had precipitated out was filtered off. After adding 2.3 ml (0.018 mmol) of N-ethylmorpholine, 6.25 g (0.015 mol) of the product from Example 48, dissolved in 50 ml of tetrahydrofuran, were added dropwise. After a further 4 h, working up took place by adding ethyl acetate, washing with 0.1N HCl and saturated NaCl solution, drying and concentrating. The crude product was further purified by chromatography on silica gel (tert-butyl methyl ether). Yield: 8.9 g of the N-tert-butoxycarbonyl-protected product as an oil.

b) Elimination of the protective group

Elimination of the protective group, and conversion into the hydrochloride, were effected by treating with trifluoroacetic acid (25 ml) in dichloromethane (150 ml), concentrating and evaporating down several times after adding ethereal hydrochloric acid, followed by thorough stirring with petroleum ether. Yield: 6.3 g of amorphous hydrochloride.

EXAMPLE 56

(3-(3-(4-Hydroxy-3,5-di-tert-butylphenyl)isoxazol-5-ylmethyl)ureido)acetic acid 6.5 g (0.015 mol) of the product from Example 54 were hydrolyzed in analogy with Example 3. Yield: 5.7 g

EXAMPLE 57

Diethyl 2-(3-(4-hydroxy-3,5-di-tert-butylphenyl)isoxazol-5-yl)vinylphosphonate

The reaction was carried out in absolute tetrahydrofuran, following a method in the literature (J Med Chem, 32 (1989), 2171) and proceeding from 6.4 g (0.021 mol) of the product from Example 47a), 6.25 ml (0.025 mol) of tetraethylmethylenediphosphonate and 9.6 ml (0.024 mol) of a 2.5M solution of butyllithium. After completion of the reaction, the reaction mixture was poured into ice water and extracted several times with dichloromethane; this was followed by washing with water, drying and concentration. The product was crystallized from tert-butyl methyl ether/petroleum ether. Yield: 7.9 g.

EXAMPLE 58

2-(3-(4-Hydroxy-3,5-di-tert-butylphenyl)isoxazol-5-yl)vinylphosphonic acid 4.0 g (0.009 mol) of the product from Example 57 were stirred, under a protective gas and at room temperature, in 300 ml of absolute dichloromethane together with 3.9 ml (0.03 mol) of trimethylbromosilane until the reaction was complete (monitoring by TLC). After adding 0.5 ml of water, the mixture was concentrated; the residue was taken up several times in methanol and concentrated under reduced pressure. The oil was stirred with tert-butyl methyl ether until a crystalline residue remained. Yield: 3.0 g.

EXAMPLE 59

3-(4-Hydroxy-3,5-di-tert-butylphenyl)-5-acetylisoxazole 5.0 g (0.016 mol) of the product from Example 28 were subjected to a Swern oxidation in analogy with Example 47a). Yield: 3.88 g.

EXAMPLE 60

3-(4-Pyridyl)-5-(4-hydroxy-3,5-di-tert-butylphenyl)-2-isoxazoline a) 2,6-di-tert-butyl-4-vinylphenol The synthesis of the olefin is known: (P. Grosso, O. Vogl: J. Macromol. Sci. Chem., A23 (1986), 1041–1056).

b) Hydroxamoyl chloride as nitrile oxide precursor

4-Pyridylhydroxamoyl chloride hydrochloride was prepared, in analogy with a method in the literature (Bull Soc Chim France (1962), 2215) by chlorinating pyridine-4-carbaldoxime.

c) Cycloaddition 11.6 g (0.05 mol) of the product from a) and 9.7 g (0.05 mol) of the product from Example 60b) were initially introduced in 500 ml of dichloromethane, and a solution of 20.9 ml (0.15 mol) of triethylamine in 200 ml of dichloromethane was then added dropwise within 6 hours. The working-up was carried out as in Example 1. Yield: 13.1 g.

EXAMPLE 61

3-(2-Thiazolyl)-5-(4-hydroxy-3,5-di-tert-butylphenyl)-2-isoxazoline 5 g (0.039 mol) of 2-thiazolylcarbaldoxime (preparation: A. Dondoni, Synthesis (1987), 998–1001) were chlorinated, as described in Example 1, using tert-butyl hypochlorite in dichloromethane/dimethylformamide (1:1), and 16.3 g (0.07 mol) of the olefin from Example 60a) were then added and cycloaddition took place in accordance with Example 1. The remaining oil was purified by chromatography on silica gel using tert-butyl methyl ether/petroleum ether 1:2 and crystallized from methanol/a little water. Yield: 6.4 g.

EXAMPLE 62

3-Carboxy-5-(4-hydroxy-3,5-di-tert-butylphenyl)-2-isoxazoline a) Hydroxamoyl chloride as nitrile oxide precursor Ethyl chloroxyiminoacetate was prepared from glycine ethyl ester by a method in the literature (G. S. Skinner, J Am Chem Soc, 46 (1924), 731).

b) Cycloaddition using ethoxycarbonylnitrile oxide 4.55 g (0.03 mol) of the product from Example 62a), dissolved in 80 ml of dichloromethane, were added dropwise, within 6 hours, to a solution of 4.65 g (0.02 mol) of the olefin from Example 60a) and 5.6 ml (0.04 mol) of triethylamine in 100 ml of dichloromethane. The working-up was carried out in accordance with Example 1. Yield: 4.8 g.

c) Hydrolysis of the ethyl ester

The hydrolysis and working-up were carried out in analogy with Example 3. 3.55 g of crystalline carboxylic acid were obtained from 6.0 g (0.017 mol) of the product from EXAMPLE 62b).

For the cycloaddition step of the following Examples 63 and 65, nitrobutyric acid structural components were dehydrated using isocyanates in a variant of the method of Mukaiyama (J Am Chem Soc, 82 (1960), 5339–5342). The route of synthesis, proceeding from acrylic acid derivatives and nitromethane, is representative for the derivatives which cannot be obtained commercially and which are described below for the case of tert-butyl nitrobutyrate. This method is also applicable to derivatives of 4-nitropropylphosphinic acid and 4-nitropropylphosphonic acid when correspondingly substituted esters of vinylphosphonic acid and vinylphosphinic acid are used.

EXAMPLE 63

5-(4-Hydroxy-3,5-di-tert-butylphenyl)-2-isoxazolin-3-ylpropionic acid a) tert-Butyl nitrobutyrate 537 ml (3.7 mol) of tert-butyl acrylate were added dropwise, at a bath temperature of 70° C., to an initially introduced solution of 2.0 l of nitromethane and 7 ml of 1,8-diazabicyclo[5.4.0]undec-7-ene (DBU), with the pH, which could possibly have declined due to traces of acrylic acid, being maintained constant by the addition of appropriate quantities of DBU. After the exothermic reaction had subsided (rise of temperature to 90° C.), the mixture was allowed to cool for 60 min and then washed several times with dilute aqueous hydrochloric acid and water, dried and concentrated under reduced pressure, with 660 g of a reddish-brown oil remaining which was further purified by distillation ($bp_5$: 90° C.).

The following nitro compounds were prepared by the same route: dimethyl and diethyl esters of 3-nitropropylphosphonic acid (proceeding from vinylphosphonic esters) ethyl 3-nitropropyl-P-methylphosphinate (proceeding from ethyl vinyl-P-methylphosphinate).

b) Cycloaddition 7.0 g (0.03 mol) of the olefin from Example 60a) were initially introduced, at 50° C., with 0.5 ml of triethylamine and 6.4 g (0.04 mol) of phenylene diisocyanate, cyanate, in 80 ml of toluene. 7.6 g (0.04 mol) of the tert-butyl 4-nitrobutyrate described under a), and 0.2 ml of triethylamine, were dissolved in 80 ml of toluene and added dropwise within 5 hours. The mixture was stirred at room temperature overnight; urea which had precipitated out was then filtered off with suction and washed with dichloromethane. After concentrating, an oily crude product remained which was further purified by chromatography on silica gel (eluent: petroleum ether/tert-butyl methyl ether mixture).

c) Elimination of the carboxyl protective group 5 g (0.012 mol) of the product from b) were treated, in 80 ml of dichloromethane and at room temperature, with 20 ml of trifluoroacetic acid until the reaction was complete (approximately 3 hours). After concentrating, the residue was stirred thoroughly with tert-butyl methyl ether, with 3.6 g of a crystalline product being obtained.

EXAMPLE 64

5-(4-Hydroxy-3,5-di-tert-butyl)phenyl-2-isoxazoline-3-propionic acid-N-(1H-tetrazol-5-yl) amide 5.0 g (0.15 mol) of the product from Example 63 were derivatized, in accordance with Example 38, using silicon tetrachloride and 5-aminotetrazole in absolute pyridine. The product was crystallized from tert-butyl methyl ether/petroleum ether. Yield: 3.5 g.

EXAMPLE 65

(2-(5-(4-Hydroxy-3,5-di-tert-butylphenyl)-2-isoxazolin-3-yl)ethyl)methylphosphinic acid The cycloaddition was carried out in accordance with Example 63, proceeding from ethyl 3-nitropropyl-P-methylphosphinate. The phosphinic ester group was cleaved in accordance with Example 7 under alkaline conditions.

EXAMPLE 70

L-Phenylalanine-1-(3-(4-hydroxy-3,5-di-tert-butylphenyl)isoxazol-5-yl)ethyl ester hydrochloride a) Acylation using N-tert-butoxycarbonylphenylalanine 2.65 g (0.01 mol) of N-tert-butoxycarbonylphenylalanine were dissolved in 50 ml of anhydrous tetrahydrofuran, 1.53 g (0.01 mol) of 1-hydroxybenzotriazole hydrate and 2.27 g (0.011 mol) of dicyclohexylcarbodiimide were then added, and the mixture was stirred for about 45 min. After adding 0.12 g of 4-dimethylaminopyridine, 3.17 g (0.01 mol) of the product from Example 28, dissolved in 25 ml of tetrahydrofuran, were added dropwise. After a further 2 h, working-up took place as follows: addition of ethyl acetate, washing with 0.1N NaOH, 0.1N HCl and saturated NaCl solution, drying and concentration. The crude product was further purified by chromatography on silica gel (petroleum ether/tert-butyl methyl ether 5:1).

Yield: 3.15 g of the N-tert-butoxycarbonyl-protected product.

b) Elimination of the protective group

Elimination of the protective group, and conversion into the hydrochloride, were effected by treating with trifluoroacetic acid (10 ml) in dichloromethane (50 ml), concentrating, and evaporating down several times after adding ethereal HCl, followed by thorough stirring with tert-butyl methyl ether/petroleum ether. Yield: 2.2 g.

EXAMPLES 71 AND 72

L-Phenylalanine-1-(3-(4-hydroxy-3,5-di-tert-butylphenyl)isoxazol-5-yl)ethyl ester hydrochloride a) Elimination of the protective group 3.0 g of the product from Example 70a) were treated with trifluoroacetic acid (analogous to Example 70b). Yield: 2.8 g of crude product.

b) Resolution of the isomers

The crude product was resolved into the diastereomers by being chromatographed several times on silica gel using dichloromethane/tert-butyl methyl ether 1:10 in the presence of 1% triethylamine. Yield: in each case 0.7–0.8 g of oily product, designated below as isomer A (higher $R_f$ value) and B (lower $R_f$ value). The purity, determined by HPLC, was in each case more than 95%. Both isomers were converted into the hydrochlorides as described in Example 70b). It was possible to crystallize each of the isomers from dichloromethane/tert-butyl methyl ether.

Example 71 (isomer A): $[\alpha]_D^{20}=+56.1°$ (c=1 in ethanol)
Example 72 (isomer B): $[\alpha]_D^{20}=-30.8°$ (c=1 in ethanol)

EXAMPLE 73

L-Phenylalanine-1-(3-(4-hydroxy-3,5-di-tert-butylphenyl)-2-isoxazolin-5-yl)ethyl ester hydrochloride a) Acylation using N-tert-butoxycarbonylphenylalanine The synthesis was effected in accordance with Example 70a) proceeding from 3.2 g (0.01 mol) of the product from Example 19 (rac. erythro isomer).

Yield: 3.5 g of the N-tert-butoxycarbonyl-protected product.

b) Elimination of the protective group

The protective group was cleaved in analogy with Example 70b). Yield: 2.6 g of the isomer mixture (due to the use of racemic isoxazoline).

EXAMPLES 74 AND 75

L-Phenylalanine-1-(3-(4-hydroxy-3,5-di-tert-butylphenyl)isoxazolin-5-yl)ethyl ester hydrochloride a) Resolution of the isomers 2.5 g of the product from Example 73a) were resolved into the diastereomers by being chromatographed repeatedly on silica gel using petroleum ether/tert-butyl methyl ether 5:1. Yield: in each case, 0.6–0.7 g of oily product, designated below as isomer A (higher $R_f$ value) and B (lower $R_f$ value). The purity, determined by HPLC, was in each case more than 95%.

b) Elimination of the protective group

Elimination of the protective group and conversion into the hydrochloride were effected for both isomers as described in Example 70b).

Example 74 (isomer A): $[\alpha]_D^{20}=+31.6°$ (c=1 in ethanol)
Example 75 (isomer B): $[\alpha]_D^{20}=-59.7°$ (c=1 in ethanol)

EXAMPLE 76

Glycine-1-(3-(4-hydroxy-3,5-di-tert-butylphenyl) isoxazol-5-yl)ethyl ester hydrochloride The synthesis was carried out in accordance with Example 70, proceeding from 2.1 g (0.012 mol) of N-BOC-glycine and 3.2 g (0.01 mol) of the product from Example 28. Following elimination of the protective group and conversion into the hydrochloride, an amorphous solid product was obtained from tert-butyl methyl ether/petroleum ether. Yield: 2.6 g

EXAMPLE 77

Glycine-1-(3-(4-hydroxy-3,5-di-tert-butylphenyl)-2-isoxazoline-5-yl)ethyl ester hydrochloride The synthesis was carried out in accordance with Example 70, proceeding from 2.1 g (0.012 mol) of N-BOC-glycine and 3.2 g (0.01 mol) of the product from Example 19 (rac. erythro isomer). Following elimination of the protective group and conversion into the hydrochloride, an amorphous solid product was obtained from tert-butyl methyl ether/petroleum ether. Yield: 2.3 g.

EXAMPLE 81

1-(3-(4-Hydroxy-3,5-di-tert-butylphenyl)-2-isoxazolin-5-yl)ethyl hexadecanoate (erythro isomer)

3.2 g (0.01 mol) of the product from Example 19 were dissolved in 60 ml of tetrahydrofuran. After adding 125 mg of 4-dimethylaminopyridine and 3.05 ml (0.024 mol) of N-ethylmorpholine, 5.5 g (0.02 mol) of hexadecanoyl chloride, dissolved in 30 ml of tetrahydrofuran, were added dropwise, while cooling with ice; after completion of the reaction (monitoring by TLC), the mixture was washed with water, aqueous potassium hydrogen sulfate solution and water, dried and concentrated. The remaining oil was purified by chromatography on silica gel using petroleum ether/tert-butyl methyl ether. Yield: 1.9 g

EXAMPLE 82

Di-O-acetyl-L-tartaric acid-N-(3-(4-hydroxy-3,5-di-tert-butylphenyl)isoxazol-5-yl)methylamide 4.2 g (0.01 mol) of the product from Example 48 were initially introduced, together with 0.12 g of 4-dimethylaminopyridine and 4.5 ml (0.035 mol) of N-ethylmorpholine, in 250 ml of tetrahydrofuran, and 3.3 g (0.015 mol) of (+)-di-O-acetyl-L-tartaric anhydride, dissolved in 60 ml of tetrahydrofuran, were added dropwise, at room temperature and while stirring, within 0.5 hours. After a further 4 h at room temperature, 50 ml of 1N HCl, 500 ml of water and 500 ml of ethyl acetate were added; after the phases had been separated, washing took place with water and saturated NaCl solution, followed by drying and concentration. The residue was chromatographed on silica gel using tert-butyl methyl ether, and subsequently crystallized from tert-butyl methyl ether/petroleum ether. Yield: 4.9 g: $[\alpha]_D^{20}=-1.4°$ (c=1 in ethanol)

EXAMPLE 83

N-[(3-(4-Hydroxy-3,5-di-tert-butylphenyl)isoxazol-5-yl)methyl]-L-tartaramide 1.56 g (0.03 mol) of the product from Example 82 were dissolved in 200 ml of methanol, and 0.84 g (0.06 mol) of finely ground potassium carbonate was added. The mixture was stirred overnight, acidified with aqueous citric acid and extracted several times with ethyl acetate. The oil which remained after drying and concentrating by evaporation was crystallized.

Yield: 1.25 g: $[\alpha]_D^{20}=+21.5°$ (c=1 in ethanol)

EXAMPLE 84

1-(3-(4-Hydroxy-3,5-di-tert-butylphenyl)-2-isoxazolin-5-yl)ethyl 3-oxobutyrate 1.6 g of the product from Example 19 were dissolved, together with approx. 15 mg of 4-dimethylaminopyridine, and while cooling with ice, in 80 ml of abs. tetrahydrofuran, and 0.46 ml (0.006 mol) of diketene, dissolved in 15 ml of tetrahydrofuran, was added dropwise. After 1 h, the ice bath was removed and the mixture was stirred at room temperature overnight. After the mixture had been concentrated down, the residue was taken up in water/ethyl acetate and the organic phase was dried and concentrated. After that, crystallization took place from tert-butyl methyl ether/ petroleum ether.

Yield: 1.05 g of pale yellow crystals.

EXAMPLE 85

Diphenyl 1-(3-(4-hydroxy-3,5-di-tert-butylphenyl)-2-isoxazolin-5-yl)ethyl phosphate 3.2 g (0.01 mol) of the product from Example 19 were dissolved, together with 0.12 g of 4-dimethylaminopyridine and 1.4 ml (11 mmol) of N-ethylmorpholine, in 60 ml of abs. tetrahydrofuran, and 2.95 g (11 mmol) of diphenyl chlorophosphate, dissolved in 10 ml of tetrahydrofuran, were added dropwise at room temperature. After 4 h, aqueous citric acid and ethyl acetate were added, the organic phase was dried and concentrated, and the residue was crystallized.

Yield: 4.7 g of crystalline product.

EXAMPLES 86 AND 87

1-(3-(4-Hydroxy-3,5-di-tert-butylphenyl)-2-isoxazolin-5-yl)ethyl 4-(4-morpholino) methylbenzoate hydrochloride, 86: erythro and 87: threo isomer a) 4-Chloromethylbenzoylbut-3-en-2-yl ester 7.2 g (0.1 mol) of rac. 1-buten-3-ol are stirred for 24 h, together with 20.5 g (0.108 mol) of 4-chloromethylbenzoyl chloride, 14 g (0.11 mol) of N-ethylmorpholine and 1.2 g of 4-dimethylaminopyridine, in 200 ml of abs. tetrahydrofuran. After dichloromethane and aqueous citric acid had been added, the phases were separated and the org. phase was washed with water, dried and concentrated. Digestion took place with petroleum ether and small quantities of a precipitated solid were removed by filtration. Following concentration, the product was isolated as an oil.

b) The reaction was carried out in analogy with Example 1), proceeding from 7.5 g (0.03 mol) of aldoxime and 7.6 g (0.034 mol) of the product from Example 86a). The crude product, which was initially in the form of an oil, was subjected to further purification by chromatography on silica gel (petroleum ether/ethyl acetate 9:1).

Yield: 3.7 g of a rac. erythro/threo isomeric mixture.

c) Reaction with morpholine 3.6 g (7.6 mmol) of the product resulting from b) were dissolved in acetone, 1.3 ml (0.015 mol) of morpholine and 0.27 g (1.6 mmol) of potassium iodide were added and the mixture was stirred at room temperature for 2 days. Following concentration, the residue was taken up in water/ ethyl acetate, and the organic phase was washed with water, dried and concentrated. 4 g of the product remained as a diastereomeric mixture (isomer ratio, approx. 60:40).

d) Isomer resolution

The crude product from c) was dissolved in approx. 200 ml of tert-butyl methyl ether, and 8 ml of 5-molar ethanolic hydrochloric acid and approx. 30 ml of dichloromethane were added. The precipitated hydrochloride was isolated and recrystallized from isopropanol, with the erythro diastereomer crystallizing out first; this diastereomer was then enriched to a diastereomer ratio of >95:5 by means of additional crystallizations from isopropanol.

Yield: 0.75 g.

It was also possible to isolate the threo diastereomer from the pooled mother liquors by means of repeated crystallization.

EXAMPLE 88

L-Tyrosyl 1-(3-(3,5-di-tert-butyl-4-hydroxyphenyl)-2-isoxazolin-5-yl)ethyl ester, rac. 5,5'-erythro isomer mixture a) Acylation with N,O-di-tert-butoxycarbonyl-L-tyrosine 7.6 g (0.02 mol) of N,O-di-tert-butoxycarbonyl-L-tyrosine were dissolved in 100 ml of anhydrous tetrahydrofuran, and 2.7 g (0.02 mol) of 1-hydroxybenzotriazole and 4.5 g (0.022 mol) of dicyclohexylcarbodiimide were added; the mixture was then stirred for approx. 45 min and precipitated urea was removed by filtration. After 2.3 ml (0.018 mol) of N-ethylmorpholine and 0.24 g (0.002 mol) of dimethylaminopyridine had been added, 4.8 g (0.015 mol) of the product from Example 19, dissolved in 80 ml of tetrahydrofuran, were added dropwise. After the mixture had been stirred at room temperature for 24 h, working-up was effected by adding ethyl acetate, washing with 0.1N NaOH and 0.1N HCl and a saturated solution of NaCl, drying and concentrating. The crude product was subjected to further purification by chromatography on silica gel (tert-butyl methyl ether/petroleum ether).

Yield: 10.5 g of the N-tert-butoxycarbonyl-protected product as an oil.

b) Elimination of the protecting group

The protecting group was eliminated in analogy with Example 70b). After the base had been liberated, further purification was carried out by means of chromatography on silica gel (tert-butyl methyl ether/dichloromethane/ methanol, 10:9:1).

Yield: 1.6 g of an amorphous solid.

EXAMPLE 89

3-(3,5-Di-tert-butyl-4-hydroxyphenyl)-5-(1,2-dihydroxyethyl)-2-isoxazoline, rac. erythro isomer 2.9 g of the product from Exp. 16 were dissolved in 50 ml of dioxane and 10 ml of water, after which 0.75 ml of 70% aqueous perchloric acid was added and the mixture was stirred at room temperature for 18 h. After 20 ml of a 5% aqueous solution of sodium carbonate and 150 ml of water had been added, the mixture was extracted repeatedly with ethyl acetate and the organic phase was washed, dried and concentrated. The product was obtained in pure form by crystallization from tert-butyl methyl ether/petroleum ether.

Yield: 1.3 g.

EXAMPLE 90

3-(3,5-Di-tert-butyl-4-hydroxyphenyl)-5-(1,2-dihydroxyethyl)-2-isoxazoline, rac. threo isomer Implementation was effected in analogy with Exp. 89, proceeding from 2.4 g of product from Exp. 17.

Yield: 1.25 g of crystalline product.

EXAMPLE 91

1-(3-(4-Hydroxy-3,5-di-tert-butylphenyl)-2-isoxazolin-5-yl)ethyl 4-(4-methylpiperazin-1-ylmethylbenzoate dihydrobromide, erythro isomer Implementation was effected in analogy with Exp. 86. The diastereomers were enriched at step b) by means of fractional crystallization. In step c), N-methylpiperazine was used in place of morpholine. After the hydrobromides had been precipitated, the isomeric enrichment at step d) was >95%.

Yield: 1.9 g of erythro product, proceeding from 4.7 g of step b).

TABLE 1

| Example | Structure | Solvent | ¹H NMR | M.p. (°C.) |
|---|---|---|---|---|
| 1 | 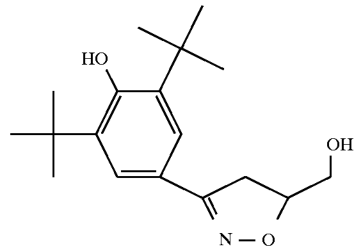 | CDCl₃ | 1.45(s, 18H) 2.05(tb, 1H) 3.16–3.45(m, 2H) 3.55–3.95(m, 2H) 4.83(m, 1H) 5.49(s, 1H) 7.5(s, 2H) | 132–135 |
| 2 | 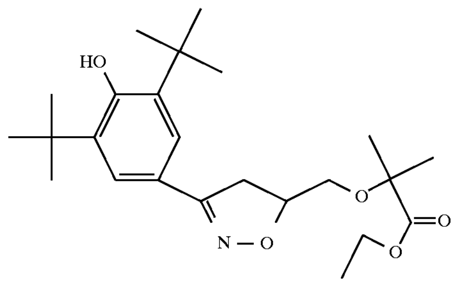 | CDCl₃ | 1.26(t, 3H) 1.43–1.46(sb, 24H) 3.3–3.68(m, 4H) 4.18(q, 2H) 4.86(m, 1H) 5.49(s, 1H) 7.52(s, 2H) | 86–88 |
| 3 | 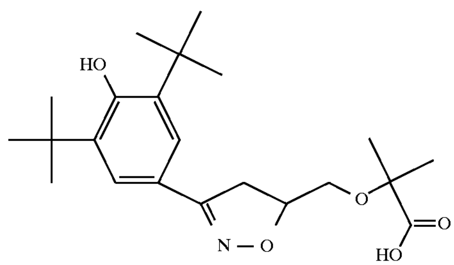 | CDCl₃ | 1.46(s, 18H) 1.48 and 1.50(in each case s, 3H) 3.15–3.52(m, 2H) 3.61(d, 2H) 4.89(m, 1H) 5.50(s, 1H) 7.50(s, 2H) | 183–186 |
| 4 | 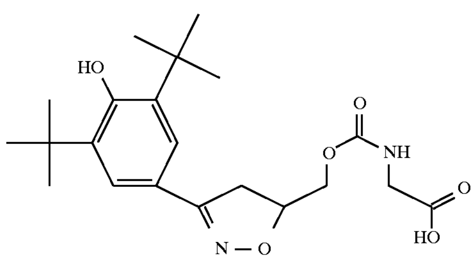 | CDCl₃ | 1.39(s, 18H) 3.05–3.70(m, 4H) 3.95–4.19(m, 2H) 4.82(m, 1H) 7.40(s, 2H) 7.58(tb, 1H) | 124–132 |
| 5 | 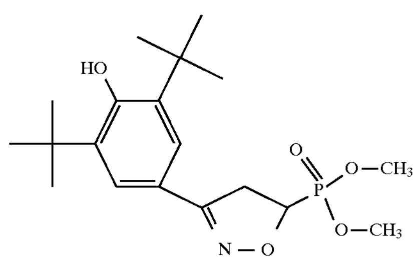 | CDCl₃ | 1.45(s, 18H) 3.58–3.78(m, 2H) 3.82–3.95(2d, in each case 3H) 4.88(m, 1H) 5.52(sb, 2H) 7.50(s, 2H) | 196 |
| 6 | 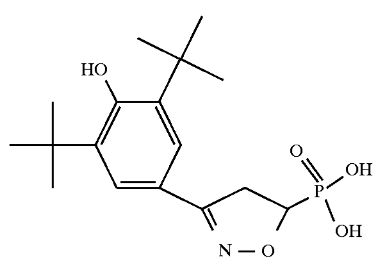 | DMSO-d6 | 1.39(s, 18H) 3.25–3.85(m, 2H) 4.62(m, 1H) 7.39(s, 2H) 11.0(sb, 2H) | 214 (decomp.) |

TABLE 1-continued

| Example | Structure | Solvent | ¹H NMR | M.p. (°C.) |
|---|---|---|---|---|
| 7 | 3,5-di-tert-butyl-4-hydroxyphenyl C(=N-OH)-CH₂-CH(P(=O)(OCH₃)₂) | DMSO-d6 | 1.39(s, 18H) 3.25–3.95(m, 5H, incl. d, 3H at 3.65) 4.76(m, 1H) 7.40(s, 2H) 7.48(sb, 1H) | 183–186 (decomp.) |
| 8 | 3,5-di-tert-butyl-4-hydroxyphenyl C(=N-OH)-CH₂-CH(2-thienyl) | DMSO-d6 | 1.39(s, 18H) 3.34–3.86(m, 2H) 5.70(m, 1H) 7.13(m, 1H) 7.40–7.58(m, 4H) | 121–125 |
| 9 | 3,5-di-tert-butyl-4-hydroxyphenyl C(=N-OH)-CH₂-CH(2-pyridyl) | DMSO-d6 | 1.39(s, 18H) 3.59–3.94(m, 2H) 5.72(m, 1H) 7.30–7.55(m, 5H) 7.82(m, 1H) 8.57(m, 1H) | 149–150 |
| 10 | 3,5-di-tert-butyl-4-hydroxyphenyl C(=N-OH)-CH₂-CH(4-pyridyl) | DMSO-d6 | 1.39(s, 18H) 3.29–3.44 and 3.82–4.0(in each case m, 1H) 5.73(m, 1H) 7.35–7.47(m, 5H) 8.57(m, 2H) | 179–180 |
| 11 | 3,5-di-tert-butyl-4-hydroxyphenyl C(=N-OH)-CH₂-CH(C(=O)NH₂) | DMSO-d6 | 1.39(s, 18H) 3.40–3.75(m, 2H) 4.99(m, 1H) 7.41(s, 2H) 7.44(sb, 1H) 7.60(sb, 1H) | 258–262 |
| 12 | 3,5-di-tert-butyl-4-hydroxyphenyl C(=N-OH)-CH₂-cyclopropyl | CDCl₃ | 0.81(m, 2H) 1.21(m, 2H) 1.46(s, 18H) 3.41(s, 2H) 5.47(s, 1H) 7.50(s, 2H) | 149–151 |

TABLE 1-continued

| Example | Structure | Solvent | ¹H NMR | M.p. (°C.) |
|---|---|---|---|---|
| 13 | 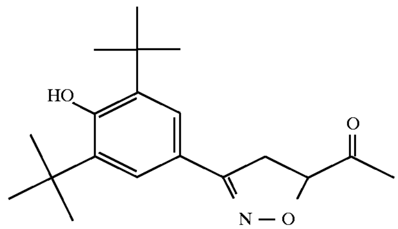 | CDCl₃ | 1.40(s, 18H)<br>2.31(s, 3H)<br>3.35–3.64(m, 2H)<br>4.94(m, 1H)<br>5.47(s, 1H)<br>7.45(s, 2H) | 94 |
| 14 | 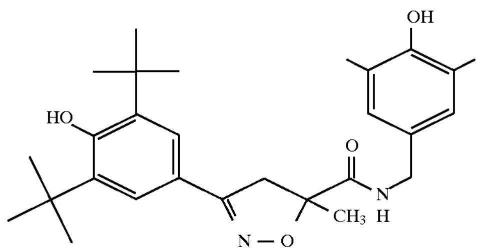 | CDCl₃ | 1.44(s, 18H)<br>1.74(s, 3H)<br>2.18(s, 6H)<br>3.24(d, 1H)<br>3.88(d, 1H)<br>4.14–4.43(m, 2H)<br>4.70(s, 1H)<br>5.52(s, 1H)<br>6.84(s, 2H)<br>7.13(tb, 1H)<br>7.47(s, 2H) | 194 |
| 15 | 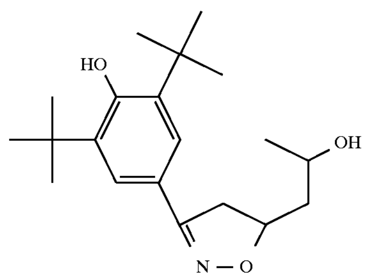 | CDCl₃ | 1.34–1.28(2d, 3H)<br>1.45(s, 18H)<br>1.58–2.04(m, 3H)<br>2.93–3.10 and<br>3.38–3.58(in<br>each case m, 1H)<br>4.12 and 4.90(in<br>each case m, 1H)<br>5.47 and 5.48(in<br>each case s,<br>0.5H)<br>7.49 and 7.50(in<br>each case s, 1H) | 131–133 |
| 16 | 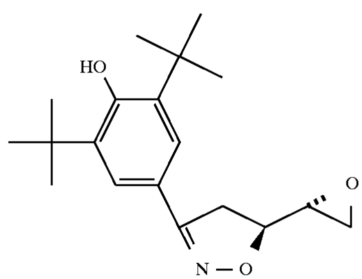 | CDCl₃ | 1.46(s, 18H)<br>2.72, 2.89 and<br>3.16(in each<br>case m, 1H)<br>3.21–3.52(m, 2H)<br>4.61(m, 1H)<br>5.50(s, 1H)<br>7.51(s, 2H) | 148–153 |
| 17 | 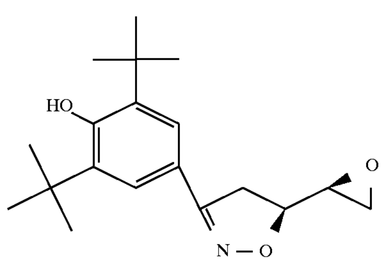 | CDCl₃ | 1.45(s, 18H)<br>2.84(d, 2H)<br>3.18–3.57(m, 3H)<br>4.73(m, 1H)<br>5.48(s, 1H)<br>7.49(s, 2H) | 123–126 |
| 18 | 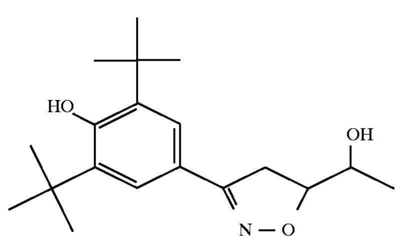 | DMSO-d6 | 1.06–1.11(2d, 3H)<br>1.40(s, 18H)<br>3.08–3.43(m, 2H)<br>3.52–3.80(m, 1H)<br>4.31–4.55(m, 1H)<br>4.81–4.96(2db, 1H), OH)<br>7.36(sb, 1H)<br>7.40 and 7.41(in each case s, 1H) | 126–146 |

| Example | Structure | Solvent | ¹H NMR | M.p. (°C.) |
|---|---|---|---|---|
| 19 | 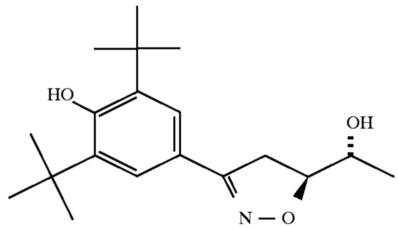 | DMSO-d6 | 1.07(d, 3H)<br>1.39(s, 18H)<br>3.15–3.41(m, 3H)<br>3.62(m, 1H)<br>4.38(m, 1H)<br>4.90(d, 1H)<br>7.38(s, 2H) | 161 |
| 20 | 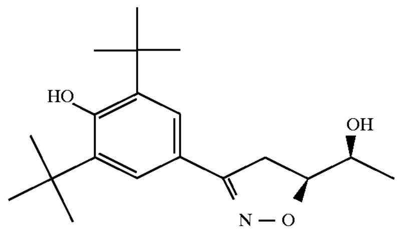 | DMSO-d6 | 1.07(d, 3H)<br>1.38(s, 18H)<br>3.05–3.45(m, 3H)<br>3.66(m, 1H)<br>4.44(m, 1H)<br>4.85(d, 1H)<br>7.38(s, 2H) | 134–135 |
| 21 | 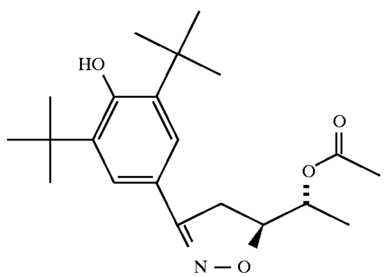 | CDCl₃ | 1.30(d, 3H)<br>1.46(s, 18H)<br>2.07(s, 3H)<br>3.05–3.50(m, 2H)<br>4.72(m, 1H)<br>5.07(m, 1H)<br>5.48(s, 1H)<br>7.49(s, 2H) | 149–151 |
| 22 | 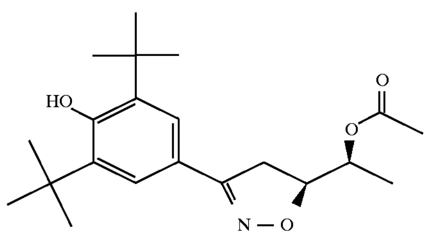 | CDCl₃ | 1.32(d, 3H)<br>1.46(s, 18H)<br>2.06(s, 3H)<br>3.02–3.48(m, 2H)<br>4.73(m, 1H)<br>5.09(m, 1H)<br>5.48(s, 1H)<br>7.49(s, 2H) | 128–130 |
| 23 | 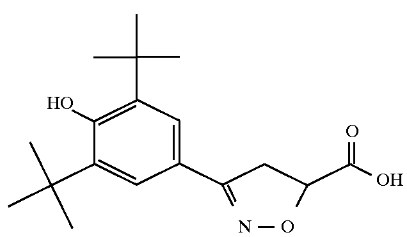 | MeOH–d4 | 1.44(s, 18H)<br>3.50–3.85(m, 2H)<br>4.93(sb, acid H)<br>5.13(m, 1H)<br>7.50(s, 2H) | 176–178 (decomp.) |
| 24 | 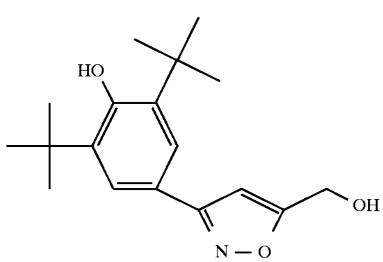 | MeOH–d4 | 1.47(s, 18H)<br>4.70(s, 2H)<br>4.88(sb, acid H)<br>6.67(s, 1H)<br>7.62(s, 2H) | 149–155 |

TABLE 1-continued

| Example | Structure | Solvent | ¹H NMR | M.p. (°C.) |
|---|---|---|---|---|
| 25 | 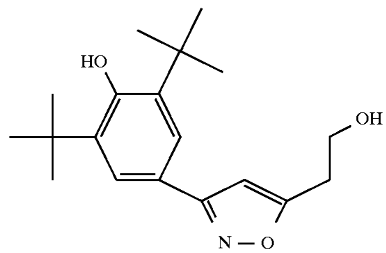 | DMSO-d6 | 1.42(s, 18H)<br>2.92(t, 2H)<br>3.75(m, 2H)<br>4.90(tb, 1H)<br>6.72(s, 1H)<br>7.33(sb, 1H)<br>7.54(s, 2H) | 125 |
| 26 | 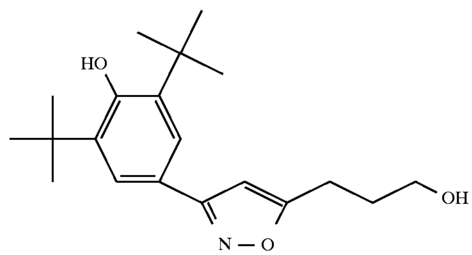 | CDCl₃ | 1.48(s, 18H)<br>2.02(m, 2H)<br>2.91(t, 2H)<br>3.75(t, 2H)<br>5.43(s, 1H)<br>6.26(s, 1H)<br>7.59(s, 2H) | 133–135 |
| 27 | 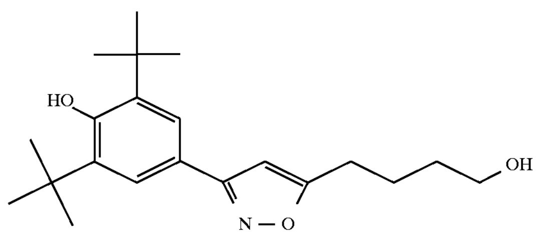 | DMSO-d6 | 1.3–1.59(m, 20H)<br>1.71(m, 2H)<br>2.77(t, 2H)<br>3.41(m, 2H)<br>4.45(tb, 1H)<br>6.71(s, 1H)<br>7.35(sb, 1H)<br>7.54(s, 2H) | 82 |
| 28 | 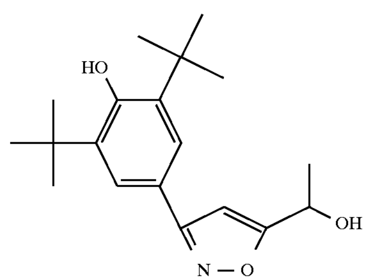 | DMSO-d6 | 1.36–1.53(s, 18H and d, 3H)<br>4.89(m, 1H)<br>5.75(db, 1H)<br>6.79(s, 1H)<br>7.38(sb, 1H)<br>7.56(s, 2H) | 123–124 |
| 29 | 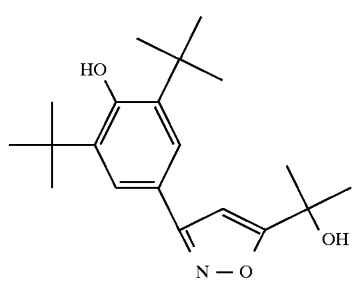 | DMSO-d6 | 1.43(s, 18H)<br>1.52(s, 6H)<br>5.62(sb, 1H)<br>6.74(s, 1H)<br>7.36(sb, 1H)<br>7.55(s, 2H) | 142 |

TABLE 1-continued

| Example | Structure | Solvent | ¹H NMR | M.p. (°C.) |
|---|---|---|---|---|
| 30 | 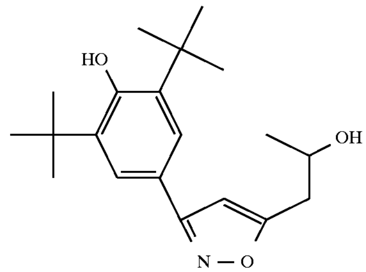 | CDCl₃ | 1.32(d, 3H)<br>1.48(s, 18H)<br>1.80(db, 1H)<br>2.95(d, 2H)<br>4.24(m, 1H)<br>5.44(s, 1H)<br>6.36(s, 1H)<br>7.60(s, 2H) | 125–132 |
| 31 | 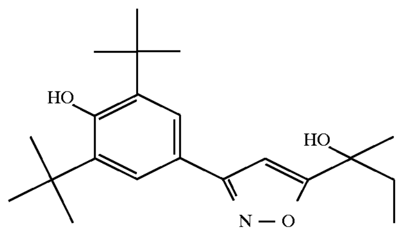 | DMSO-d6 | 0.82(t, 3H)<br>1.44(s, 18H)<br>1.48(s, 3H)<br>1.80(q, 2H)<br>5.50(sb, 1H)<br>6.74(s, 1H)<br>7.35(sb, 1H)<br>7.57(s, 2H) | 150–151 |
| 32 | 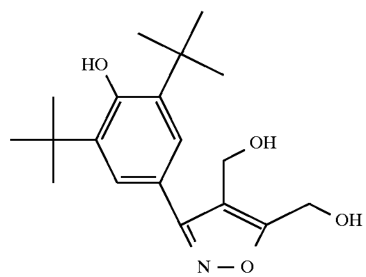 | DMSO-d6 | 1,43(s, 18H)<br>4.41 and 4.63(in each case d, 2H)<br>5.11 and 5.52(in each case tb, 1H)<br>7.34(sb, 1H)<br>7.66(s, 2H) | 191–195 (decomp.) |
| 33 | 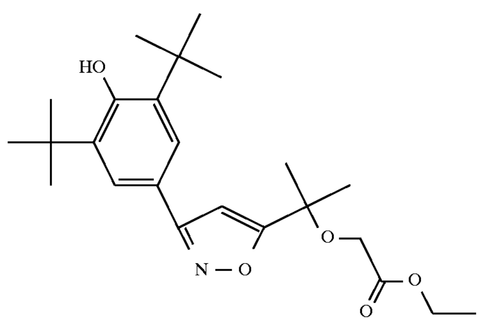 | CDCl₃ | 1.33(t, 3H)<br>1.45(s, 18H)<br>1.68(s, 6H)<br>2.19(sb, 1H)<br>4.32(q, 2H)<br>4.37(s, 2H)<br>6.43(s, 1H)<br>7.67(s, 2H) | 124 |
| 34 | 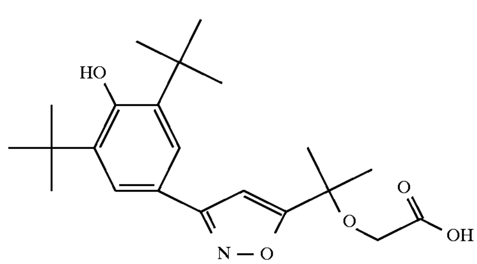 | DMSO-d6 | 1.42(s, 18H)<br>1.53(s, 6H)<br>4.30(s, 2H)<br>5.65(sb, 1H)<br>6.91(s, 1H)<br>7.72(s, 2H)<br>13.1(sb, 1H) | 209–210 |

TABLE 1-continued

| Example | Structure | Solvent | ¹H NMR | M.p. (°C.) |
|---|---|---|---|---|
| 35 | 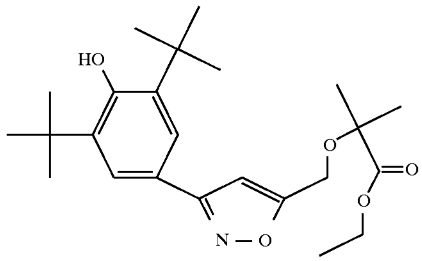 | CDCl₃ | 1.30(t, 3H) 1.47(s, 18H) 1.53(s, 6H) 4.23(q, 2H) 4.65(s, 2H) 5.48(s, 1H) 6.54(s, 1H) 7.61(s, 2H) | 67–68 |
| 36 | 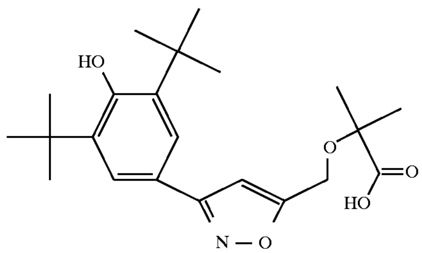 | CDCl₃ | 1.48(s, 18H) 1.59(s, 6H) 4.70(s, 2H) 5.45(sb, 1H) 6.54(s, 1H) 7.61(s, 2H) | 182–185 |
| 37 | 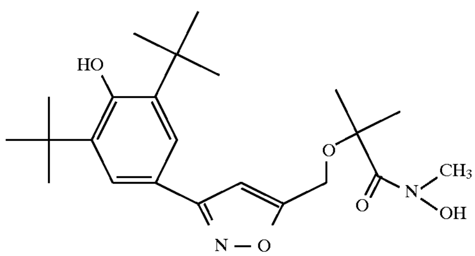 | CDCl₃ | 1.48(s, 18H) 1.59(s, 6H) 3.60(sb, 3H) 4.53(sb, 2H) 5.47(sb, 1H) 6.50(s, 1H) 7.60(s, 2H) 8.50(sb, 1H) | 107–113 |
| 38 | 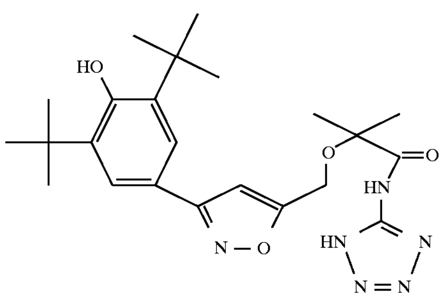 | DMSO-d6 | 1.43(s, 18H) 1.54(2, 6H) 4.69(sb, 2H) 6.99(s, 1H) 7.41(sb, 1H) 7.56(s, 2H) 11.80(sb, 1H) | 247–249 (decomp.) |
| 39 | 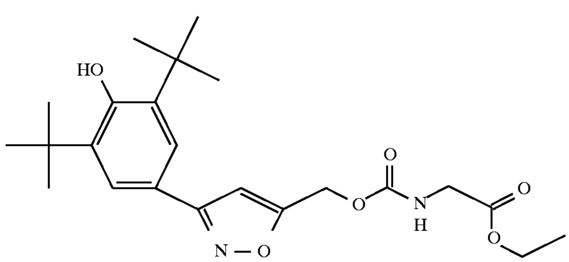 | CDCl₃ | 1.28(t, 3H) 1.47(s, 18H) 3.98(d, 2H) 4.21(q, 2H) 5.23(sb, 2H) 5.40(tb, 1H) 5.46(s, 1H) 6.58(s, 1H) 7.60(s, 2H) | (oil) |

TABLE 1-continued

| Example | Structure | Solvent | ¹H NMR | M.p. (°C.) |
|---|---|---|---|---|
| 40 | 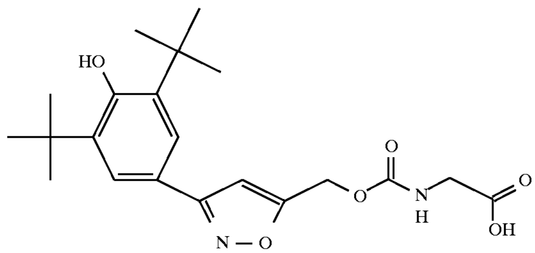 | DMSO-d6 | 1.43(s, 18H)<br>3.40(sb, 2H)<br>3.71(d, 2H)<br>5.20(sb, 2H)<br>6.99(s, 1H)<br>7.56(s, 2H)<br>7.80(tb, 1H)<br>12.65(sb, 1H) | 185–188 |
| 41 | 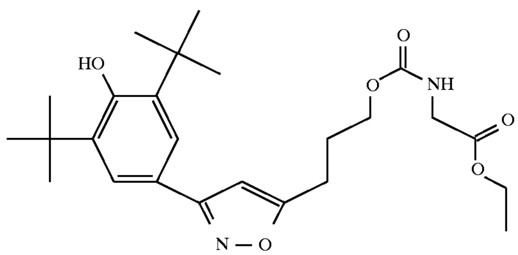 | CDCl$_3$ | 1.29(t, 3H)<br>1.48(s, 18H)<br>2.10(m, 2H)<br>2.88(t, 2H)<br>3.98(d, 2H)<br>4.11–4.30(m, 4H)<br>5.20(tb, 1H)<br>5.44(s, 1H)<br>6.27(s, 1H)<br>7.59(s, 2H) | 86 |
| 42 | 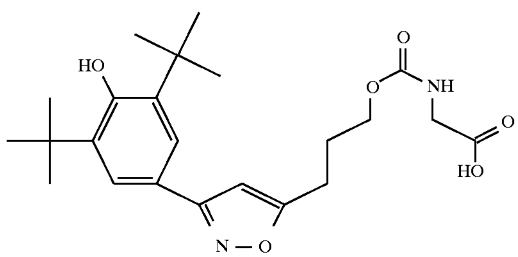 | DMSO-d6 | 1.43(s, 18H)<br>1.99(m, 2H)<br>2.82(tb, 2H)<br>3.67(d, 2H)<br>4.06(tb, 2H)<br>6.77(s, 1H)<br>7.33(sb, 1H)<br>7.45(tb, 1H)<br>7.55(s, 2H)<br>12.55(sb, 1H) | 201–203 |
| 43 | 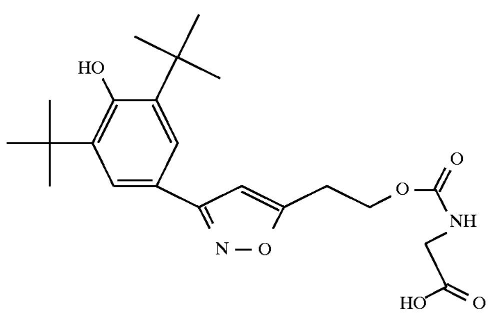 | DMSO-d6 | 1.42(s, 18H)<br>3.10(tb, 2H)<br>3.63(d, 2H)<br>4.29(tb, 2H)<br>6.80(s, 1H)<br>7.35(sb, 1H)<br>7.54(s, 2H and tb, 1H)<br>12.55(sb, 1H) | 152–155 |
| 44 | 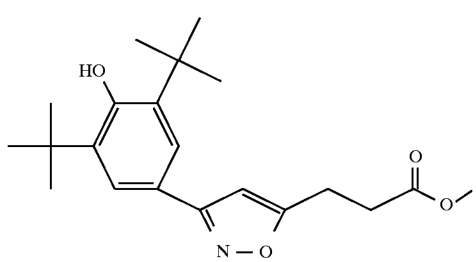 | CDCl$_3$ | 1.48(s, 18H)<br>2.79 and 3.12(in each case t, 2H)<br>3.71(s, 3H)<br>5.43(s, 1H)<br>6.28(s, 1H)<br>7.58(s, 2H) | 89 |

TABLE 1-continued

| Example | Structure | Solvent | ¹H NMR | M.p. (°C.) |
|---|---|---|---|---|
| 45 | 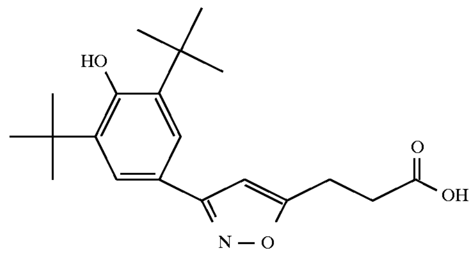 | DMSO-d6 | 1.42(s, 18H) 2.71 and 2.99(in each case t, 2H) 6.75(s, 1H) 7.35(sb, 1H) 7.54(s, 2H) 12.4(sb, 1H) | 188 |
| 46 | 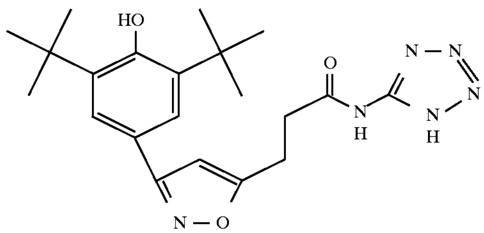 | DMSO-d6 | 1.43(s, 18H) 2.95 and 3.15(in each case tb, 2H) 6.75(s, 1H) 7.38(s, 1H) 7.54(s, 2H) 12.2(sb, 1H) | 249 (decomp.) |
| 47 | 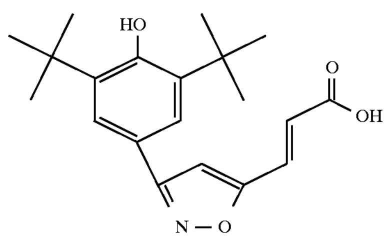 | DMSO-d6 | 1.44(s, 18H) 6.65 and 7.51(in each case d, 1H) 7.49(s, 1H) 7.60(s, 2H) 13.0(sb, 1H) | 206–208 |
| 48 | 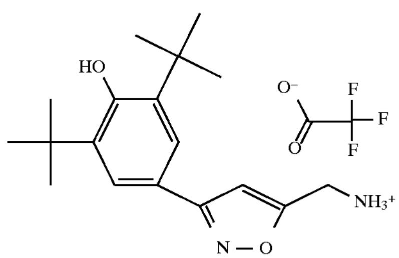 | DMSO-d6 | 1.43(s, 18H) 4.33(s, 2H) 7.06(s, 1H) 7.52(sb, 1H) 7.55(s, 2H) 8.65(sb, acid H) | 194 |
| 49 | 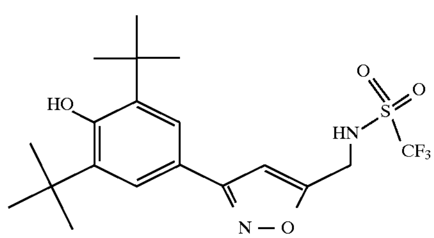 | CDCl₃ | 1.48(s, 18H) 4.60(s, 2H) 5.51(s, 1H) 6.55(s, 1H) 7.58(s, 2H) | 163–165 |
| 50 | 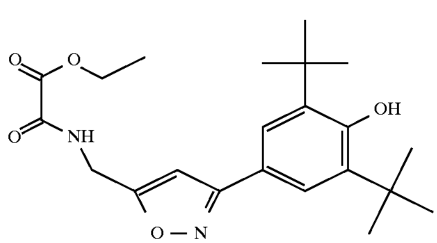 | CDCl₃ | 1.35–1.50(s, 18H) and t, 3H) 4.38(q, 2H) 4.69(d, 2H) 5.46(s, 1H) 6.49(s, 1H) 7.55(s and tb, 3H) | 124–126 |

TABLE 1-continued

| Example | Structure | Solvent | ¹H NMR | M.p. (°C.) |
|---|---|---|---|---|
| 51 | 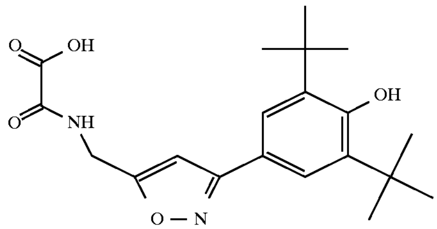 | DMSO-d6 | 1.41(s, 18H)<br>4.48(d, 2H)<br>6.81(s, 1H)<br>7.40(sb, 1H)<br>7.55(s, 2H)<br>9.50(tb, 1H)<br>13.7(sb, 1H) | 165 (decomp.) |
| 52 | 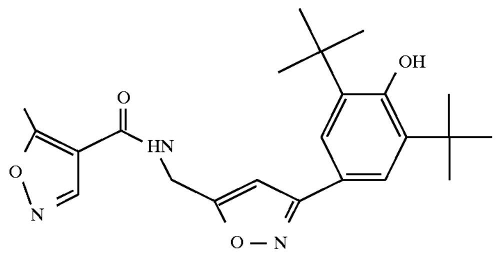 | CDCl₃ | 1.46(s, 18H)<br>2.73(s, 3H)<br>4.72(d, 2H)<br>5.47(s, 1H)<br>6.51(s, 1H and tb, 1H)<br>7.57(s, 2H)<br>8.41(s, 1H) | 146–148 |
| 53 | 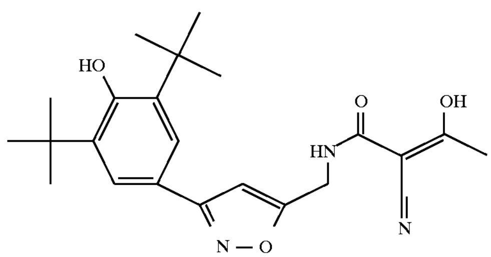 | CDCl₃ | 1.47(s, 18H)<br>2.31(s, 3H)<br>4.67(d, 2H)<br>5.46(s, 1H)<br>6.46(s, 1H)<br>6.51(tb, 1H)<br>7.58(s, 2H)<br>15.3(sb, 1H) | 178–180 |
| 54 | 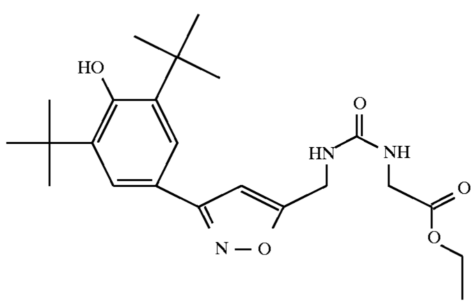 | CDCl₃ | 1.25(t, 3H)<br>1.46(s, 18H)<br>4.0(d, 2H)<br>4.18(q, 2H)<br>4.54(d, 2H)<br>5.38(tb, 1H)<br>5.45(s, 1H)<br>5.54(tb, 1H)<br>6.47(s, 1H)<br>7.57(s, 2H) | 145–150 |
| 55 | 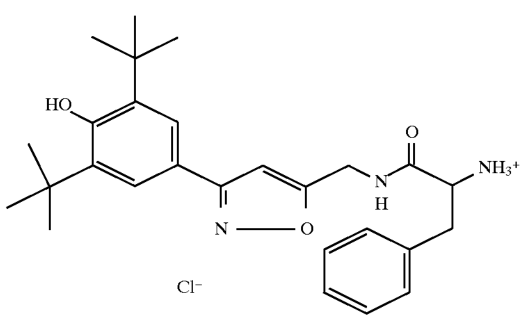 | DMSO-d6 | 1.44(s, 18H)<br>3.0–3.22(m, 2H)<br>4.07(tb, 1H)<br>4.45(db, 2H)<br>6.75(s, 1H)<br>7.15–7.35(m, 5H)<br>7.54(s, 2H)<br>8.05(sb, acid H)<br>9.35(tb, 1H) | 98–138 (amorphous) |

TABLE 1-continued

| Example | Structure | Solvent | ¹H NMR | M.p. (°C.) |
|---|---|---|---|---|
| 56 | 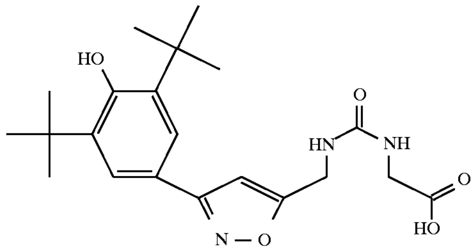 | DMSO-d6 | 1.42(s, 18H) 3.73(d, 2H) 4.37(d, 2H) 6.40(tb, 1H) 6.68(s, 1H) 6.85(tb, 1H) 7.40(sb, 1H) 7.53(s, 2H) | 159–165 |
| 57 | 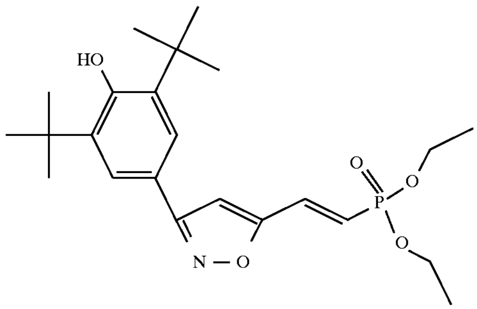 | DMSO-d6 | 1.29(t, 6H) 1.43(s, 18H) 4.0–4.15(m, 2H) 6.75(t, 1H) 7.35(dd, 1H) 7.47(d, 1H) 7.59(s, 2H) | 119–125 |
| 58 | 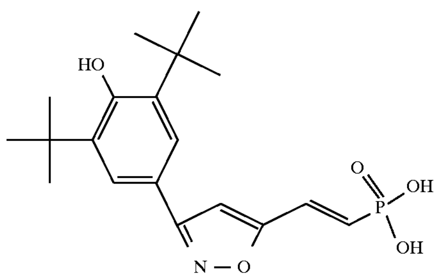 | DMSO-d6 | 1.44(s, 18H) 6.68(dd, 1H) 7.15(dd, 1H) 7.39(s, 1H) 7.60(s, 2H) 9.3–10.0(sb, acid H) | 247–249 (decomp.) |
| 59 | 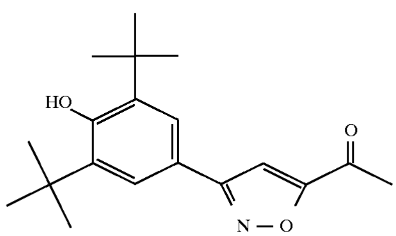 | CDCl₃ | 1.49(s, 18H) 2.65(s, 3H) 5.53(s, 1H) 7.17(s, 1H) 7.64(s, 2H) | 161–162 |
| 60 | 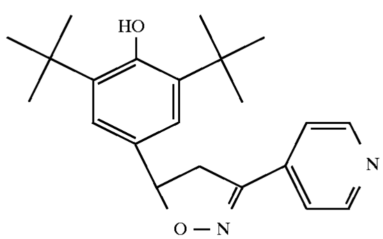 | CDCl₃ | 1.44(s, 18H) 3.25–3.41 and 3.60–3.75(in each case m, 1H) 5.31(s, 1H) 5.71(m, 1H) 7.17(s, 2H) 7.57 and 8.70(in each case m, 2H) | 191–193 |
| 61 | 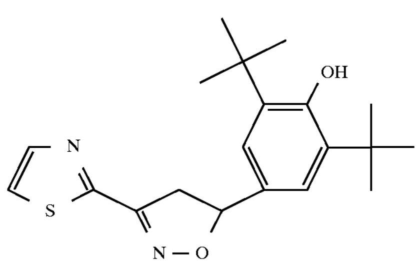 | DMSO-d6 | 1.39(s, 18H) 3.35–3.55 and 3.81–3.99(in each case m, 1H) 5.73(m, 1H) 7.11(s, 1H) 7.16(s, 2H) 7.92 and 8.02(in each case d, 2H) | 89–91 |

TABLE 1-continued

| Example | Structure | Solvent | ¹H NMR | M.p. (°C.) |
|---|---|---|---|---|
| 62 | 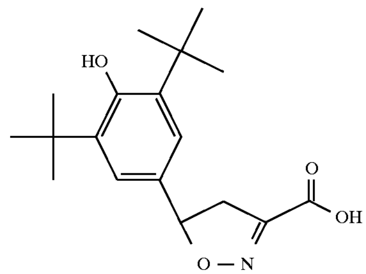 | CDCl₃ | 1.44(s, 18H) 3.17–3.33 and 3.51–3.67(in each case m, 1H) 5.33(sb, 1H) 5.78(m, 1H) 7.13(s, 2H) 6.7–7.5(sb, acid H) | 151–153 |
| 63 | 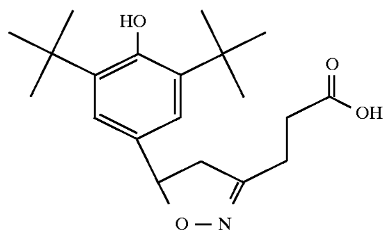 | CDCl₃ | 1.43(s, 18H) 2.60–2.82(m, 4H) 2.90–3.05 and 3.20–3.38(in each case m, 1H) 5.25(sb, 1H) 5.49(m, 1H) 7.13(s, 2H) 6.1–7.6(sb, acid H) | 171–174 |
| 64 | 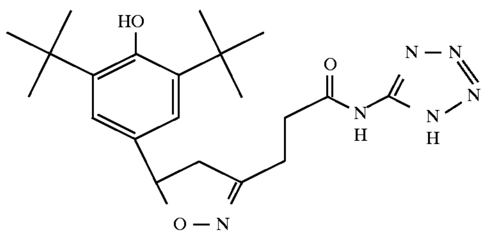 | CDCl₃ | 1.20(s, 18H) 2.47–2.88(m, 5H) 3.06–3.25(m, 1H) 4.25(sb, acid H) 5.28(m, 1H) 6.89(s, 2H) | 220–224 |
| 65 | 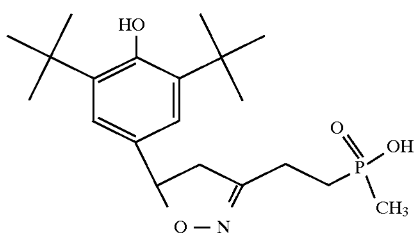 | CDCl₃ | 1.43(s, 18H) 1.53(d, 3H) 2.0–2.21(m, 2H) 2.55–2.79(m, 2H) 2.90–3.05 and 3.20–3.39(in each case m, 1H) 5.35(sb, acid H) 5.48(m, 1H) 7.13(s, 2H) | 182–184 (decomp.) |
| 66 | 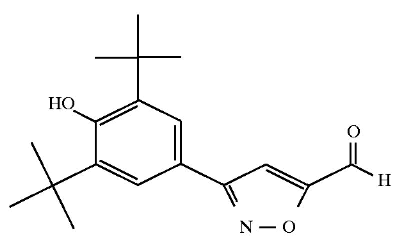 | CDCl₃ | 1.49(s, 18H) 5.54(s, 1H) 7.25(s, 2H) 10.02(s, 1H) | 127 |
| 67 | 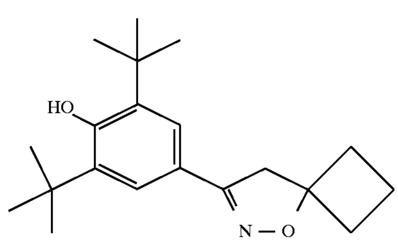 | CDCl₃ | 1.35–1.95(m, 2H and s, 18H) 2.1–2.3(m, 2H) 2.45–2.67(m, 2H) 3.39(s, 2H) 5.46(s, 1H) 7.49(s, 2H) | 121–122 |

| Example | Structure | Solvent | ¹H NMR | M.p. (°C.) |
|---|---|---|---|---|
| 68 | 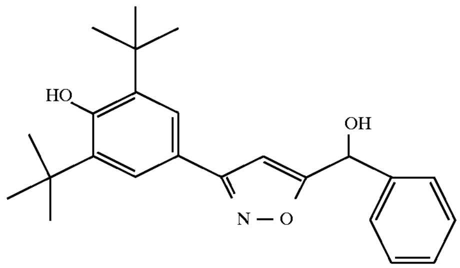 | CDCl₃ | 1.47(s, 18H)<br>2.8(sb, 1H)<br>5.45(sb, 1H)<br>5.95(s, 1H)<br>6.44(s, 1H)<br>7.3–7.5(m, 5H)<br>7.59(s, 2H) | 140 |
| 69 | 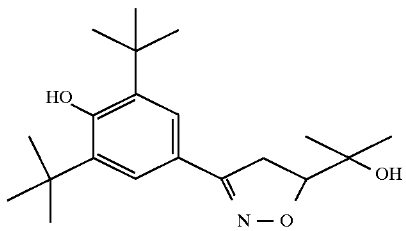 | CDCl₃ | 1.23 and 1.35(in each case s, 3H)<br>1.45(s, 18H)<br>2.06(sb, 1H)<br>3.15–3.43(m, 2H)<br>4.53(m, 1H)<br>5.48(sb, 1H)<br>7.50(s, 2H) | 139 |
| 70 | 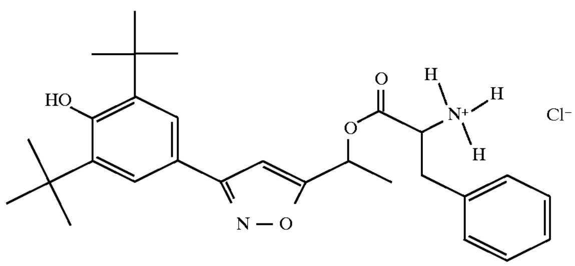 | DMSO-d6 | 1.3–1.65(2s, 18H) and 2d, 3H)<br>2.95–3.3(m, 2H)<br>4.42(tb, 1H)<br>5.9–6.13(m, 1H)<br>6.98 and 7.02 (2s, 1H)<br>7.1–7.55(m, 5H and 2s, 2H)<br>8.4(sb, 3H) | 105–125 (decomp.) |
| 71 | 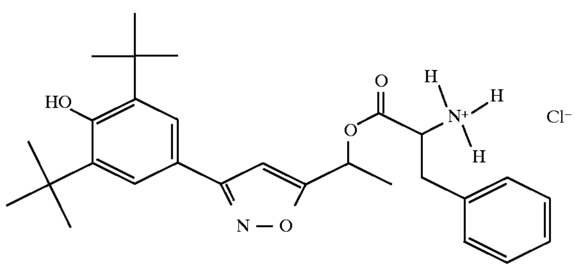 | DMSO-d6 | 1.3–1.45(s, 18H and d, 3H)<br>3.04–3.3(m, 2H)<br>4.38(tb, 1H)<br>5.93–6.08(m, 1H)<br>7.11(s, 1H)<br>7.28–7.41(m, 5H)<br>7.56(s, 2H)<br>8.4(sb, 3H) | 105–115 (decomp.) |
| 72 | 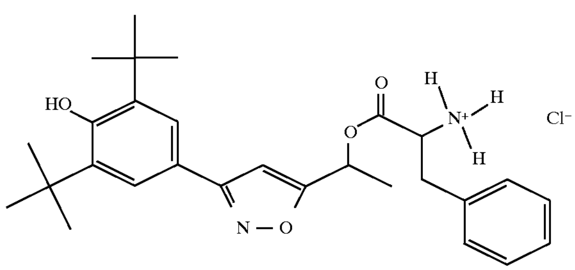 | DMSO-d6 | 1.43(s, 18H)<br>1.63(d, 3H)<br>3.0–3.25(m, 2H)<br>4.41(tb, 1H)<br>6.05–6.14(m, 1H)<br>7.0(s, 1H)<br>7.1–7.28(m, 5H)<br>7.56(s, 2H)<br>8.72(sb, 3H) | 190 |

| Example | Structure | Solvent | ¹H NMR | M.p. (°C.) |
|---|---|---|---|---|
| 73 | 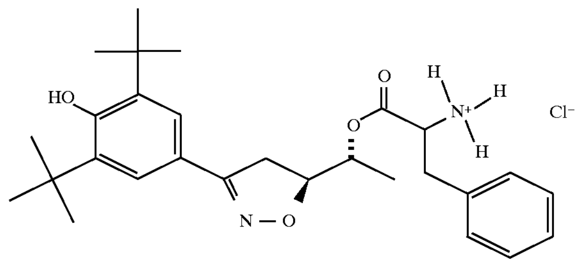 | DMSO-d6 | 1.02 and 1.23(in each case d, 1.5H) 1.35 and 1.40(in each case s, 9H) 2.85–3.57(m, 4H) 4.1–4.3(m, 1H) 4.54–4.78(m, 1H) 4.95–5.15(m, 1H) 7.1–7.48(m, 5H and 2d, in each case 1H) 8.55(sb, 3H) | 210–215 |
| 74 | 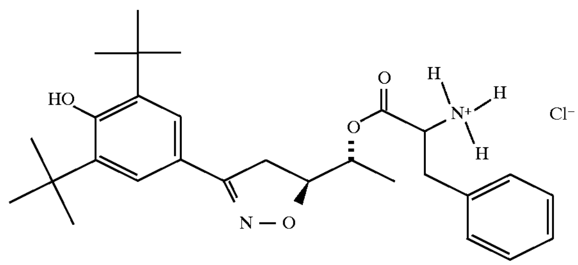 | DMSO-d6 | 1.02(d, 3H) 1.40(s, 18H) 2.90–3.50(m, 4H) 4.1–4.25(m, 1H) 4.58–4.73(m, 1H) 4.90–5.04(m, 1H) 7.1–7.31(m, 5H) 7.37(s, 2H) 8.79(sb, 3H) | 207 |
| 75 | 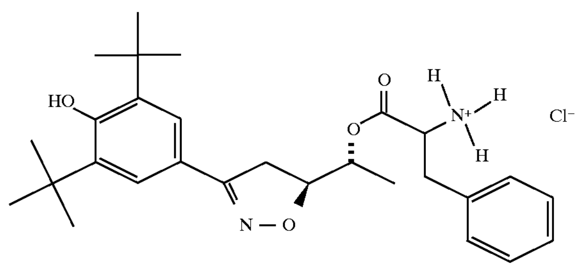 | DMSO-d6 | 1.23(d, 3H) 1.35(s, 18H) 2.95–3.06(d, 2H) 3.20–3.57(m, 2H) 4.25(t, 1H) 4.63–4.78(m, 1H) 5.08–5.15(m, 1H) 7.1–7.3(m, 5H) 7.38(s, 2H) 8.40(sb, 3H) | 193 |
| 76 | 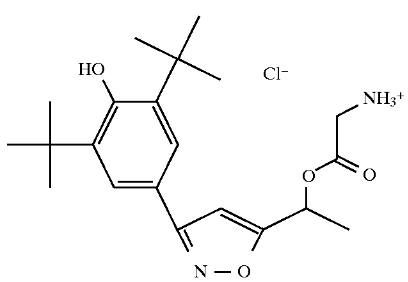 | DMSO-d6 | 1.43(s, 18H) 1.66(d, 3H) 3.93(sb, 2H) 6.13(q, 1H) 7.17(s, 1H) 7.45(sb, 1H) 7.57(s, 2H) 8.60(sb, 3H) | 70–85 (decomp.) |
| 77 | 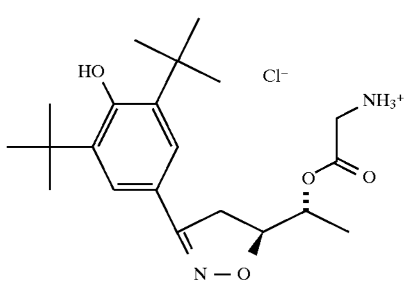 | DMSO-d6 | 1.23(d, 3H) 1.40(s, 18H) 3.22–3.90(m, 4H) 4.65–4.85(m, 1H) 5.0–5.18(m, 1H) 7.40(s, 2H) 7.47(sb, 1H) 8.40(sb, 3H) | 90–110 (decomp.) |

TABLE 1-continued

| Example | Structure | Solvent | ¹H NMR | M.p. (°C.) |
|---|---|---|---|---|
| 78 | 3,5-di-tert-butyl-4-hydroxyphenyl group with C(=N-O)-CH2-CH(OH)-CH2-CH2-CH(OH)-CH3 side chain | CDCl₃ | 1.22(d, 3H) 1.45(s, 18H) 1.50–2.05(m, 4H) 2.97–3.12 and 3.40–3.57(in each case m, 1H) 3.2–3.8(sb, 2H) 4.0–4.28(m, 2H) 4.82–5.02(m, 1H) 5.50(s, 1H) 7.49(s, 2H) | 144–145 |
| 79 | 3,5-di-tert-butyl-4-hydroxyphenyl group with C(=N-O)-CH2-CH(OMe)-CH2-CH(OH)-CH2-CH=CH2 side chain | CDCl₃ | 1.45(s, 18H) 1.50–2.0(m, 2H) 2.2–2.35(m, 2H) 2.6(sb, 1H) 3.07–3.16 and 3.40–3.56(in each case m, 1H) 3.85–4.05(m, 1H) 4.8–5.0(m, 1H) 5.08–5.23(m, 2H) 5.50(s, 1H) 5.7–5.95(m, 1H) 7.49(s, 2H) | 103–105 |
| 80 | 3,5-di-tert-butyl-4-hydroxyphenyl group with C(=N-O)-CH2-CH(OMe)-CH2-CH(OH)-CH2-CH=CH2 side chain (stereoisomer) | CDCl₃ | 1.45(s, 18H) 1.55–2.45(m, 5H) 2.95–3.10 and 3.40–3.56(in each case m, 1H) 3.91–4.05(m, 1H) 4.87–5.05(m, 1H) 5.08–5.23(m, 2H) 5.48(s, 1H) 5.7–5.95(m, 1H) 7.49(s, 2H) | 115–118 |
| 81 | 3,5-di-tert-butyl-4-hydroxyphenyl group with C(=N-O)-CH2-CH(O-C(=O)-(CH2)14-CH3)-CH(CH3)- side chain | CDCl₃ | 0.88(t, 3H) 1.15–1.7(m, 27H and s, 18H at 1.46) 2.3(t, 2H) 3.05–3.25 and 3.3–3.47(in each case m, 1H) 4.6–4.75(m, 1H) 4.98–5.12(m, 1H) 5.48(s. 1H) 7.48(s, 2H) | oil |
| 82 | 3,5-di-tert-butyl-4-hydroxyphenyl group with isoxazole ring and -CH2-NH-C(=O)-CH(OAc)-CH(OAc)-COOH side chain | CDCl₃ | 1.47(s, 18H) 2.06 and 2.21(in each case s, 3H) 4.45–4.81(m, 2H) 5.48(sb, 1H) 5.64 and 5.83(in each case d, 2H) 6.49(s, 1H) 6.85(t, 1H) 7.56(s, 2H) | 88–92 (decomp.) |

TABLE 1-continued

| Example | Structure | Solvent | ¹H NMR | M.p. (°C.) |
|---|---|---|---|---|
| 83 | 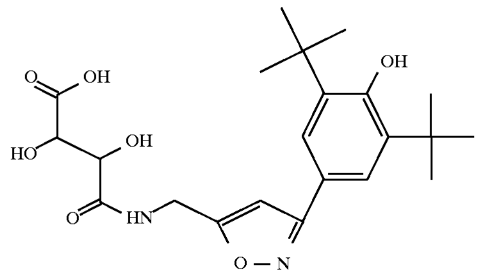 | DMSO-d6 | 1.43(s, 18H)<br>4.30–4.51(m, 4H)<br>6.69(s, 1H)<br>7.39(sb, 1H)<br>7.52(s, 2H)<br>8.48(tb, 1H) | 125–154 |
| 84 | 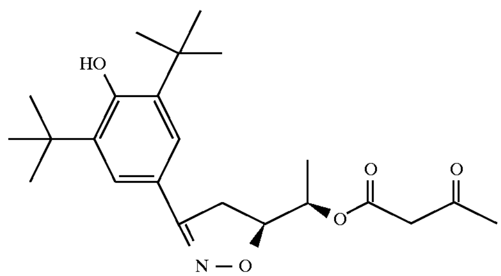 | CDCl₃ | 1.34(d, 3H)<br>1.46(s, 9H)<br>2.25(s, 3H)<br>3.13–3.49(m, 2H)<br>3.45(s, 2H)<br>4.62–4.77(m, 1H)<br>5.03–5.18(m, 1H)<br>5.49(sb, 1H)<br>7.49(s, 2H) | 102 |
| 85 | 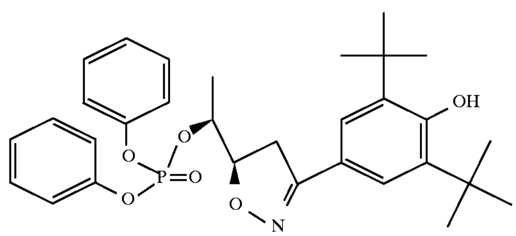 | DMSO-d6 | 1.31(d, 3H)<br>1.40(s, 18H)<br>3.18–3.60(m, 2H)<br>4.69–4.95(m, 2H)<br>7.13–7.48(m, 12H) | 118 |
| 86 | 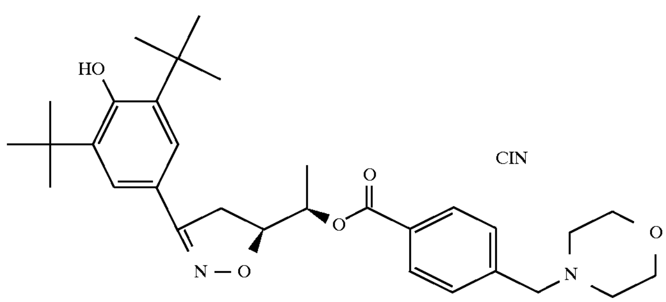 | DMSO-d6 | 1.32(d, 3H)<br>1.38(s, 18H)<br>2.95–3.98(m, 10H)<br>4.38(sb, 2H)<br>4.76–4.91(m, 1H)<br>5.19–5.28(m, 1H)<br>7.40(s, 2H)<br>7.43(sb, 1H)<br>7.73(d, 2H)<br>7.94(d, 2H)<br>11.79(sb, 1H) | 241–243<br>(decomp.) |
| 87 | 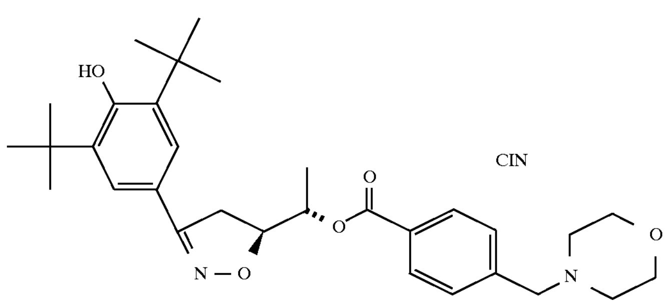 | DMSO-d6 | 1.32–1.45(d, 3H and s, 18H)<br>2.95–4.00(m, 10H)<br>4.40(db, 2H)<br>4.74–4.91(m, 1H)<br>5.09–5.23(m, 1H)<br>7.41(s, 2H)<br>7.43(sb, 1H)<br>7.76(d, 2H)<br>8.00(d, 2H)<br>11.50(sb, 1H) | 248–255<br>(decomp.) |

TABLE 1-continued

| Example | Structure | Solvent | ¹H NMR | M.p. (°C.) |
|---|---|---|---|---|
| 88 | 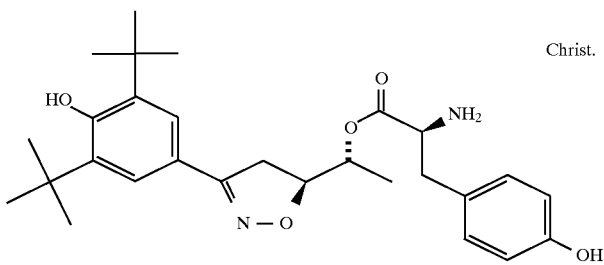 Christ. | CDCl₃ | 1.25 and 1.30(in each case d, 1.5H) 1.41 and 1.44(in each case s, 9H) 2.65–3.71(m, 5H) 4.65–4.82(m, 1H) 5.04–5.22(m, 1H) 5.49(sb, 1H) 6.55–6.68(m, 2H) 6.85–6.97(m, 2H) 7.47 and 7.49(in each case s, 1H) | 110–135 |
| 89 | 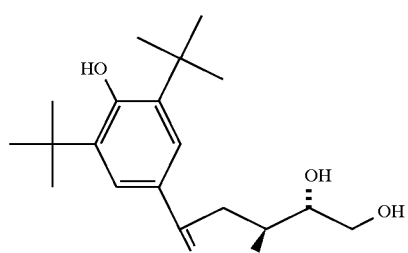 | DMSO-d6 | 1.41(s, 9H) 3.26–3.63(m, 5H) 4.52–4.71(m, 1H and sb, 1H) 5.02(d, 1H) 7.37(s, 1H) 7.41(s, 2H) | 155 |
| 90 | 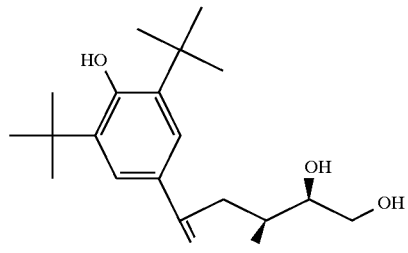 | DMSO-d6 | 1.40(s, 9H) 3.14–3.52(m, 5H) 4.56–4.72(m, 2H) 4.85(d, 1H) 7.36(s, 1H) 7.39(s, 2H) | 129 |
| 91 | 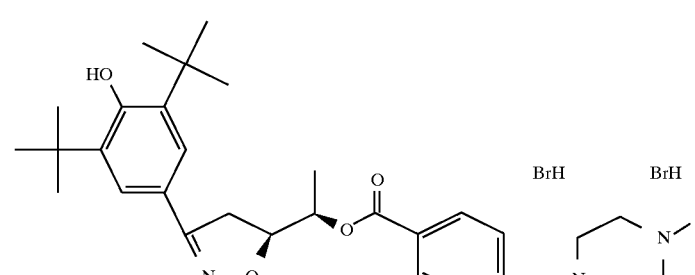 | DMSO-d6 | 1.32(d, 3H) 1.41(s, 18H) 2.87(sb, 3H) 3.10–3.68(m, 10H) 4.27(sb, 2H) 4.79–4.92(m, 1H) 5.21–5.33(m, 1H) 7.45(s, 2H) 7.47(sb, 1H) 7.61(d, 2H) 7.96(d, 2H) 10.0(sb, 1H) | 195–198 |

Pharmacological tests

In order to characterize their valuable anti-inflammatory, antiasthmatic and immunomodulatory properties, and high degree of tolerance, the compounds of the formula I were examined in the following experimental tests which are recognized as being particularly well suited for assessing the quality of effect of compounds of this type possessing antirheumatic activity.

Isolation of polymorphonuclear leucocytes (PMNL) from human peripheral blood for carrying out tests 1 and 2 10 ml of human blood were diluted with 10 ml of HBSS (Serva) and underlaid with 15 ml of Lymphoprep (Dr. Molter GmbH, Heidelberg). The sample was then centrifuged for 25 minutes at 400×g (1600 revolutions per minute, Minifuge 2, Heraeus, Osterode). This resulted in the formation of three phases: the uppermost phase is composed of plasma and thrombocytes, and the intermediate phase is Lymphoprep. A white ring, composed of mononuclear cells, is located between these two phases. The lowermost phase is composed of erythrocytes which are covered with a white layer of PMNL. The uppermost phase, and also the Lymphoprep and the white ring, were carefully removed using a syringe. The remaining sediment was carefully resuspended in 15 ml of 3% dextran in PM16 (mw: 485,000, Sigma, Deisenhofen). The suspension was then left to stand at room temperature for one hour. During this time, the erythrocytes sedimented while the PMNL remained in the supernatant. The supernatant was removed, diluted with an approximately equal volume of PM16, and centrifuged for 15 minutes at 400×g. Should the PMNL sediment be heavily contaminated with erythrocytes, it is necessary to carry out a hypotonic lysis. To do this, the sediment was resuspended in 750 µl of water. After exactly 15 seconds, the suspension was diluted with approximately 7 ml of PM16 and centrifuged for 10 minutes at 400×g. If necessary, this lysis was repeated once more. Otherwise, the PMNL sediment was resuspended in a suitable medium.

TEST 1. Release of proteolytic activity

250 µl of PMNL (5·10$^6$ cells/ml of PBS containing 7.5 mM glucose) were incubated at 37° C. for 20 minutes with 1 µl of test substance. 1 µl of cytochalasin B (5 µg/ml of test mixture) was then added and the mixture was incubated at 37° C. for a further 5 minutes. Following the addition of 1 µl of tissue necrosis factor alpha (TNF; 30 ng/ml of test mixture), the incubation was continued for 5 minutes. The release was started using 1 µl of fMLP (10 nmol/l of test mixture). After 60 minutes at 37° C., the reaction was terminated by cooling the samples down to 0° C. The samples were then centrifuged, and the supernatant was removed and frozen down. Cytochalasin B and fMLP were dissolved in DMSO and TNF was diluted with buffer. 50 µl of the supernatant were mixed with 175 µl of buffer (100 mM HEPES, pH 7.5; 500 mM NaCl) in a 96-well microtiter plate. Following the addition of 25 µl of substrate (methoxysuccinyl-L-Ala-L-Ala-L-Pro-L-Val-p-nitroanilide), the extinction of each well was measured at 405 nm after 0, 5, 10, 15, 30 and 60 minutes.

TEST 2. Release of oxygen radicals

The PMNL were resuspended (5·10$^6$ cells/ml) in Dulbecco's PBS, supplemented with 7.5 mM glucose. Care must be taken to ensure that the PMNL are free of erythrocytes. 100 µl of PMNL, 700 µl of PBS+glucose and 100 µl of cytochrome C (9.38 mg/ml of PBS+glucose) were mixed in a semi-microcuvette. 100 µl of PMNL, 500 µl of PBS+glucose, 100 µl of cytochalasin B (1·10$^6$ mol), 100 µl of TNF (0.05 ng) and 100 µl of cytochrome C (9.38 mg/ml of PBS+glucose) were mixed for the fMLP-induced release of oxygen. Measurements were made in a double-beam photometer meter (Perkin-Elmer 552 S) at a wavelength of 550 nm. The measurement range is 0–1 extinction units. The cuvettes were temperature-equilibrated to 37° C. The reference cuvette additionally contained 10 µl of SOD (6 mg of SOD/ml of PBS+glucose). Following a preincubation of 5 minutes, the reaction is started with 100 µl of inducer. The reaction is started with 1·10$^{-7}$ mol of fMLP.

TEST 3. LTB$_4$ formation by white blood cells

Isolation of white blood cells:

40 ml of human blood were mixed with 8 ml of 6% dextran solution (dextran, mw: 480,000 in PM16). After one hour at room temperature, the supernatant, which was composed of white blood cells, was removed, diluted with an equal volume of PM16, and centrifuged for 15 minutes at 300×g (1600 rpm). The sediment was next resuspended in approximately 5–6 ml of PM16 and, once the cell count had been determined in a Coulter Counter, adjusted to 10$^7$ cells/ml.

The test mixture comprised 0.24 ml of cell suspension, 0.03 ml of 20 mM CaCl$_2$/5 mM MgCl$_2$ and 5 µl of test substance. Following 15 minutes of preincubation at 37° C., the reaction was started with 0.03 ml of A23187/glutathione (100 µg of A23187/ml; 15.4 µg of glutathione/ml). The incubation was terminated after 5 minutes at 37° C. by immediate cooling of the samples down to 0° C. After centrifuging for 2 minutes in an Eppendorff Centrifuge (0° C.), the supernatant was removed and examined chromatographically.

High pressure liquid chromatography (HPLC): the HPLC equipment comprises a Kratos pump (Spectro-flow 400), a cooled automatic BT 7041 sample injector (Biotronik) having a 75 µl sample loop, a Nucleosil C$_{18}$ column (100*3 mm, 5 µm particles of Chrompack), a UV detector (Kratos) Spectroflow 757 (wavelength: 280 nm, measurement range: 0.1 AUFS, time constant: 0.5 s) and a Spectra Physics integrator (SP 4270). The eluent (725 ml of methanol, 275 ml of water and 0.1 ml of acetic acid) was supplied at a flow rate of 0.7 ml/minute and at a pressure of about 100 bar.

Notes: It has been found to be useful, before beginning the actual measurements, to measure an additional control sample. When doing this, the measurement range which has been set can be examined and altered if necessary. It is also vital to measure the test substances at the particular test concentration (e.g.: 10$^{-5}$M) in PM16 before the cell incubation, since the test substances might conceal the LTB$_4$ peak. If this is the case, a lower concentration must be selected.

Test 4. Stimulation of the cytokine release

Isolation of mononuclear cells from human blood 10 ml of human blood, stabilized with 1 ml of 3.8% sodium citrate solution, were diluted with 10 ml of PM16 (Serva, Heidelberg) and underlaid with 15 ml of Lymphoprep (Dr. Molter GmbH, Heidelberg). The samples were centrifuged, at room temperature for 40 minutes, at 400×g (1600 rpm, Minifuge 2, Heraeus, Osterode). The mononuclear cells are visible as a white ring at the Lymphoprep/plasma interface. This ring was carefully removed with a syringe, diluted with an equal volume of PM16, and centrifuged for 10 minutes at 400×g. The sediment was washed with approximately 10 ml of RPMI1640 (+300 mg/l L-glutamine, Gibco, Eggenstein) (Wallis, 1986). After the cells had been resuspended in approximately 1 ml of RPMI1640 (+300 mg/l L-glutamine+25 mM HEPES+100 µg/ml streptomycin+100 µg/ml penicillin), the cell density was determined using a Coulter Counter JT (Coulter Diagnostics) and adjusted to 5*10$^6$/ml. Typically, the cells are composed of 90% lymphocytes and 10% monocytes.

230 µl of mononuclear cells were incubated, at 37° C.; 5% CO$_2$ for 20–22 hours (5 hours in the case of IL-6), with 10 µl of test substance (10 µM in DMSO/water, 1/10) and 10 µl of lipopolysaccharide (LPS; 500 µg dissolved in 1 ml of DMSO and diluted 1/10 with water prior to beginning the test; from Salmonella abortus equi, Sigma, Deisenhofen). The samples were cooled down to 0° C. in an ice bath and centrifuged in a Sigma centrifuge (2 minutes; 2000 rpm). Aliquots of the supernatant are measured with an ELISA (Biermann, Bad Nauheim). The abbreviation IL stands for interleukin and TNF for tumor necrosis factor alpha.

TEST 5. Cyclooxygenase-dependent thrombocyte aggregation

Platelet-rich plasma (PRP): to inhibit coagulation, human blood was treated with 1/10 of its volume of 3.8% sodium citrate solution. Centrifugation then takes place at 105×g for 20 minutes and the supernatant (PRP) is removed. 200 µl of PRP were preincubated, at 37° C. for 10 minutes, together with 30 µl of test substance in a PAP4 aggregometer (BioData). The test substance was dissolved in organic solvent and diluted 1:30 with buffer (50 mM TisHCl, pH 8.0; 90 mM NaCl). Aggregation is triggered with 20 µl of inducer. During the aggregation, stirring takes place at 800 rpm. Arachidonic acid, 5 mg/ml, was used as the inducer.

The results of tests 1 to 3 are summarized in Table 2. The values in the table show the concentration of the test substance which was employed in µM and, besides this, the residual activity measured in percent based on the control, which was set to be 100%. The interleukin is additionally indicated in test 4.

TABLE 2

| Ex. | Test 1 | Test 2 | Test 3 | Test 4 | Test 5 |
|---|---|---|---|---|---|
| 1 | | | 10 μM 92 | | 10 μM 93 |
| 3 | | | | | 100 μM 98 |
| 5 | | | | | 100 μM 98 |
| 7 | | | | | 100 μM 95 |
| 8 | | | 10 μM 15<br>1 μM 93 | | 100 μM 91 |
| 9 | 100 μM 64 | | 10 μM 0<br>1 μM 59 | IL-1<br>  10 μM 73<br>IL-6<br>  10 μM 93<br>TNFα<br>  10 μM 63 | 100 μM 92 |
| 10 | | | 10 μM 20<br>1 μM 89 | TNFα<br>  10 μM 78 | 100 μM 98 |
| 13 | 100 μM 20<br>10 μM 77 | 25 μM 22<br>10 μM 65 | | | 10 μM 98 |
| 14 | | | | | 10 μM 100 |
| 18 | | | | IL-1α<br>  100 μM 36<br>  10 μM 89 | |
| 19 | 100 μM 20<br>10 μM 78 | 10 μM 94 | | | 10 μM 100 |
| 20 | | | | | 10 μM 100 |
| 24 | | | | IL-1<br>  10 μM 86 | 10 μM 94 |
| 25 | | | 10 μM 29<br>1 μM 85 | IL-1α<br>  10 μM 62<br>ILβ<br>  10 μM 93<br>TNFα<br>  10 μM 82 | 10 μM 86 |
| 26 | | | | TNFα<br>  10 μM 88 | 10 μM 94 |
| 27 | | | | | 100 μM 97 |
| 28 | 10 μM 59<br>1 μM 97 | 25 μM 8<br>10 μM 60 | 10 μM 0<br>1 μM 14 | IL-1α<br>  10 μM 93 | 10 μM 93 |
| 31 | | | | | 100 μM 100 |
| 32 | 100 μM 34<br>10 μM 72<br>1 μM 84 | | | | |
| 34 | | | | | 100 μM 98 |
| 35 | | | | IL-1α<br>  10 μM 84 | 100 μM 94 |
| 36 | | | 10 μM 93 | | 100 μM 87 |
| 38 | | | | IL-1α<br>  1 μM 89<br>IL-1β<br>  1 μM 85 | 100 μM 90 |
| 39 | | | | | 100 μM 98 |
| 41 | 100 μM 78 | 50 μM 36<br>5 μM 75 | 10 μM 13 | TNFα<br>  10 μM 89 | 100 μM 95 |
| 43 | | | 10 μM 93 | | 100 μM 99 |
| 44 | | | | | 10 μM 99 |
| 45 | | | | | 100 μM 98 |
| 46 | | | | IL-1α<br>  1 μM 77<br>IL-1β<br>  1 μM 85<br>TNFα<br>  10 μM 79 | 100 μM 90 |
| 47 | 100 μM 17<br>10 μM 38<br>1 μM 85 | | | IL-1α<br>  10 μM 72<br>  1 μM 89<br>TNFα<br>  10 μM 64 | |
| 49 | 100 μM 19<br>10 μM 23<br>1 μM 88 | 50 μM 12<br>5 μM 80 | 10 μM 0<br>1 μM 90 | IL-6<br>  1 μM 91<br>TNFα<br>  10 μM 91 | |
| 57 | | | | | 100 μM 99 |
| 58 | | | | | 100 μM 99 |
| 59 | 100 μM 35<br>10 μM 61<br>1 μM 91 | 10 μM 48<br>1 μM 135 | | | |
| 60 | | | | 10 μM 88 | |
| 61 | 100 μM 80 | | | 10 μM 3  IL-1α | 100 μM 94 |
| 63 | 100 μM 66<br>10 μM 88 | 50 μM 79 | 10 μM 91 | 1 μM 94<br>TNFα<br>  10 μM 68<br>IL-1α<br>  10 μM 75<br>IL-1β<br>  10 μM 77 | |
| 64 | 100 μM 72<br>10 μM 96 | | | IL-1<br>  10 μM 68<br>  1 μM 85<br>IL-1<br>  10 μM 82 | 100 μM 97 |
| 70 | | 10 μM 22 | | | |
| 71 | 10 μM 42<br>1 μM 79 | | | | 25 μM 97 |
| 72 | 10 μM 51<br>1 μM 82 | | | | 25 μM 100 |
| 73 | | 10 μM 9<br>1 μM 100 | | | 25 μM 100 |
| 74 | 10 μM 64 | | | | 25 μM 95 |
| 75 | 10 μM 49<br>1 μM 89 | | | | 25 μM 98 |
| 76 | 100 μM 9<br>10 μM 68 | | | | 25 μM 99 |
| 77 | 100 μM 30<br>10 μM 74 | | | | 25 μM 100 |
| 78 | | | | | 50 μM 94 |
| 79 | | | | | 100 μM 96 |
| 80 | | | | | 50 μM 97 |
| 81 | | | | | 100 μM 100 |
| 82 | | | | | 100 μM 93 |
| 85 | | | | | 100 μM 94 |

Interpretation of the table using Example 9): 64% of proteolytic activity (test 1) is released following addition of 100 μl of the inhibitory substance Ex. 9). Without inhibitory substance, proteolytic activity corresponding to 100% would be released.

RESULT: The compounds according to the invention are active as inflammation inhibitors since they exhibit perceptible biological activities as inhibitors of the release of proteolytic activity (test 1) and of active oxygen (test 2), and also of leukotriene B4 synthesis (test 3), in the human leucocyte system. The release of various cytokines from mononuclear cells (test 4) in the human system is likewise inhibited. In particular, the compounds have no inhibitory effect on the cyclooxygenase-dependent human thrombocyte system (test 5). As a consequence, undesirable side effects (prolongation of the bleeding time, gastrointestinal ulcerogenesis and renal toxicity), which can be attributed to inhibition of the cyclooxygenase, are not to be expected.

Test 6: Testing for antiarthritic effect in the adjuvant/arthritis model

Male rats of a Wistar-Lewis strain (Mollegaard/Denmark) were used as experimental animals. The body weight is between 160 and 200 g. Subplantar injection of 0.1 ml of Freund's adjuvant (=6 mg of Mycobacterium butyricum suspension, Difco Lab./Detroit, Mich. USA, per ml of heavy white paraffin oil, Merck, Darmstadt) into the root of the tail resulted, on the 10th to 14th day of the experiment, in immunopathological processes and chronic inflammations, particularly in the form of arthritic and periarthritic symptoms, at other sites in the body (secondary lesions). The animals were fed ad libitum with the standard feed Altromin-R, from Altrogge, Lage, and provided with tap water. The animals were given 60 mg of codein per kg as an analgesic from the 14th day to the end of the experiment. The test substances were administered orally as a CMC suspension, in an injection volume of 1 ml/100 g of body weight, on each day (in all for 17 days), beginning on the day of the adjuvant administration. The volumes of each of the hind paws, and the body weight, were measured on the first and on the 18th day of the experiment. Diminution in the increase of paw volume, as compared with the untreated control group, served as the criterion of activity, with the two hind paws being averaged. The results are summarized in Table 3.

Test 7: Testing for antiasthmatic effect

Anesthetized guinea pigs, which were cannulated in the jugular vein to allow injection of the PAF, were used for testing for antiasthmatic effect. The test preparations were also administered intravenously (i.v.), 5 min before PAF administration, into the blood stream through the same venous cannula, or else administered intraduodenally (i.d.), 15 minutes before the PAF, through an opening in the duodenum which had been installed and cannulated surgically. The bronchial width was recorded in an overflow pneumonogram before and after administering the preparation. Evaluation: $ED_{50}$ in mg/kg i.d. as compared with the PAF-induced asthma attack. The results are summarized in Table 3.

Test 8: Inhibition of tumor cell proliferation

The tumor cell line 20-10-5S (hybridoma cell line, supplied by ATCC (American Type Culture Collection)), which produces an antibody against mouse T cells) was used for determining the antiproliferative property of test substances. The cells were cultured, at 37° C. and 5% $C_2$, under serum-free conditions in CG medium (cell-growth medium= Iscove-ATL (+albumin+transferrin+lipids); from Vitromex, Vilshofen). Only cells which were in the logarithmic phase of growth were used for the test mixture. The test substances were pipetted in various concentrations (from 1 to 50 μM), together with $4\times10^3$ 20-10-5S cells, into round-bottomed microtiter plates (total volume with medium, 200 μl). After an incubation time of 48 h (37° C. and 5% $CO_2$), 25 μl of tritiated thymidine (=0.25 μCi/test mixture, specific activity, 23 Ci/mM) were added to the plates. During the subsequent 16 h, the radioactively labeled thymidine was incorporated into the DNA of the growing cells. The samples were filtered off with suction on glass fiber filters and the incorporated radioactivity was measured using a β counter (Beta Plate System 1205 from Wallac). On the basis of the radioactivity incorporated, the $IC_{50}$ values (50% inhibition concentration) were calculated in comparison to the positive control (test mixture without test substance), and are summarized in Table 3.

TABLE 3

| Example | Test 6 Dose (mg/kg) | Test 6 Paw volume (% inhibition) | Test 7 $ED_{50}$ (mg/kg) | Test 8 $IC_{50}$ (μM) |
|---|---|---|---|---|
| 1 | 50 | 70 | 10–50 i.d. | 5–10 |
| 3 | | | | 10 |
| 4 | | | | 30 |
| 5 | | | <10 i.d. | |
| 6 | | | about 50 i.d. | |
| 7 | | | 10–30 i.d. | |
| 8 | 50 | 67 | about 10 i.d. | <5 |
| 9 | | | about 50 i.d. | |
| 11 | | | | <5 |
| 12 | 50 | 82 | | 10 |
| 13 | 50 | 84 | about 50 i.d. | 6.10 |
| 14 | | | 10–50 i.d. | |
| 15 | 50 | 60 | | 8–15 |
| 16 | | | | 30 |
| 17 | | | | 8–15 |
| 18 | | | | 5–10 |

TABLE 3-continued

| Example | Test 6 Dose (mg/kg) | Test 6 Paw volume (% inhibition) | Test 7 $ED_{50}$ (mg/kg) | Test 8 $IC_{50}$ (μM) |
|---|---|---|---|---|
| 19 | 25 | 85 | | <5 |
| 20 | 25 | 67 | about 50 i.d. | <5 |
| 22 | 50 | 74 | | |
| 24 | 50 | 43 | | <5 |
| 25 | 50 | 44 | 3–10 i.d. | <5 |
| 26 | | | | <5 |
| 27 | 50 | 71 | | <5 |
| 28 | 50 | 74 | | <5 |
| 29 | | | | <5 |
| 30 | 50 | 63 | | 5–10 |
| 33 | | | | <5 |
| 37 | | | | <5 |
| 39 | | | | 30 |
| 40 | | | 1–3 i.d. | <5 |
| 41 | | | | <5 |
| 42 | | | | 5–10 |
| 44 | | | | 5–10 |
| 45 | | | | 5–10 |
| 47 | | | 10–50 i.d. | 5–10 |
| 48 | 50 | 60 | 10–50 i.d. | 5–10 |
| 49 | | | about 50 i.d. | 5–10 |
| 52 | | | 3–10 i.d. | <5 |
| 53 | 25 | 48 | 10–50 i.d. | 8–10 |
| 54 | | | 1–3 i.d. | 5–10 |
| 55 | 50 | 47 | | <5 |
| 56 | | | about 50 i.d. | |
| 57 | | | | <5 |
| 59 | | | 1–3 i.d. | 30 |
| 66 | 25 | 59 | | <5 |
| 67 | 50 | 53 | | <5 |
| 69 | 50 | 83 | | 5–10 |
| 70 | 25 | 59 | | 5 |
| 71 | 25 | 66 | | 5–10 |
| 72 | 25 | 60 | | 5–10 |
| 73 | 50 | 73 | | |
| 74 | 25 | 60 | | 5–10 |
| 75 | 25 | 76 | | 5–10 |
| 76 | 50 | 70 | | 20 |
| 77 | 50 | 82 | | 20 |
| 78 | | | | 5–10 |
| 79 | | | | 5–10 |
| 80 | | | | 5–10 |
| 81 | 50 | 67 | | |
| 83 | 50 | 39 | | |
| 84 | 25 | 49 | | |
| 85 | | | | <5 |
| 86 | 20 | 70 | | <5 |
| 87 | 20 | 50 | | <5 |
| 88 | | | | 10 |
| 89 | 50 | 36 | | 20 |
| 90 | 50 | 36 | | 30 |

< means less than

We claim:

1. A compound of the formula I

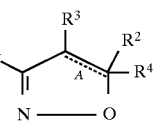

and/or a physiologically tolerated salt of the compound of the formula I and/or a stereoisomeric form of the compound of the formula I;

in this context, one radical $R^1$ or $R^2$ has the meaning of the formula II

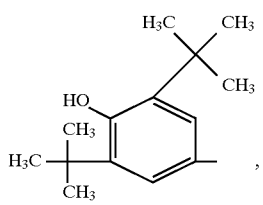

and the other radical $R^1$ or $R^2$ has the following meaning:

a) pyridyl,
b) thiophenyl,
c) thiazolyl,
d) a radical of the formula III

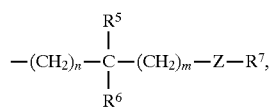

where n is the number zero, 1, 2, 3, 4, 5 or 6, m is the number zero, 1, 2, 3 or 4, Z is
1) —O—, or
2) —NH—, $R^5$ and $R^6$ are, independently of each other,
1) a hydrogen atom,
2) $(C_1-C_4)$-alkyl,
3) $(C_2-C_4)$-alkenyl,
4) $(C_2-C_4)$-alkynyl,
5) phenyl, or
6) OH, and $R^7$ is
1) a hydrogen atom,
2) residue of an amino acid,
3) trifluoromethylsulfonyl,
4) —O—P(O)(OH)$_2$,
5) —O—P(O)(OH)$_2$ mono- or diesterified with phenyl or $(C_1-C_6)$-alkyl, or
6) a radical of the formula IV

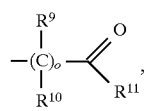

in which o is the number zero or 1, and in which $R^9$ and $R^{10}$, independently of each other, have the following meaning:
1) a hydrogen atom, or
2) $(C_1-C_4)$-alkyl, and $R^{11}$ is
1) OH,
2) —O—$(C_1-C_4)$-alkyl,
3) $(C_1-C_{20})$-alkyl,
4) $(C_1-C_{20})$-alkyl, substituted once or more than once, independently of each other, by
  4.1 —COOH,
  4.2 —OH,
  4.3 O-acetyl, or
  4.4 =O,
5) —COOH,
6)

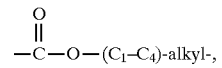

7) N-glycyl,
8) N-glycyl-$(C_1-C_4)$-alkyl ester,
9) N-$(C_1-C_4)$-alkylhydroxylamino,
10) N-(1H-tetrazol-5-yl)amino,
11) 5-methylisoxazol-4-yl,
12) 1-cyano-2-hydroxy-1-propenyl,
13) phenyl,
14) phenyl, substituted once or more than once by 14.1    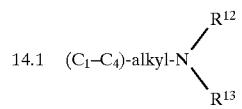

in which $R^{12}$ and $R^{13}$, independently of each other, have the following meaning:
1) a hydrogen atom,
2) $(C_1-C_4)$-alkyl,
3) phenyl-$(C_1-C_2)$-alkyl,
4) $R^{12}$ and $R^{13}$ form, together with the nitrogen atom linking them, a five- to seven-membered heterocycle which is unsubstituted or substituted once to three times by $(C_1-C_4)$-alkyl, it being possible for a carbon atom to be replaced by a sulfur, oxygen or nitrogen atom, or
5) residue of an amino acid, or $R^6$ and $R^7$ are bonded to each other and are, together, from 1 to 3 CH$_2$ radicals, e) a radical of the formula V

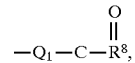

in which $Q_1$ is
1) —(CH$_2$)$_m$—, where m is the number zero, 1, 2, 3 or 4, or
2) —CH=CH—, and $R^8$ is
1) a hydrogen atom,
2) $(C_1-C_4)$-alkyl,
3) OH,
4) —O—$(C_1-C_4)$-alkyl,
5) NH$_2$,
6) N-(1H-tetrazol-5-yl)amino, or
7) N-(3,5-dimethyl-4-hydroxybenzyl)amino, or f) a radical of the formula VI

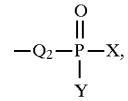

in which $Q_2$ is
1) —(CH$_2$)$_m$, where m is the number zero, 1, 2, 3 or 4, or
2) —CH=CH—, and X and Y are, independently of each other,
1) $(C_1-C_4)$-alkyl,
2) —O—$(C_1-C_4)$-alkyl, or
3) OH, ...A... is a double bond which is present or absent, with the restriction that the double bond and the radical $R^4$ are not present simultaneously, $R^4$ is
1) a hydrogen atom, or
2) $(C_1-C_6)$-alkyl, or $R^2$ and $R^4$ form, together with the carbon atom to which they are bonded, an aliphatic ring which is composed of 3, 4 or 5 carbon atoms, and $R^3$ is
1) a hydrogen atom,
2) $(C_1-C_4)$-alkyl, or
3) hydroxy-$(C_1-C_4)$-alkyl.

2. A compound of the formula I as claimed in claim 1, where one radical $R^1$ or $R^2$ has the meaning of the formula II and the other radical $R^1$ or $R^2$ has the following meaning:

a) 2-pyridyl,
b) 4-pyridyl,
c) thiophen-3-yl,
d) 2-thiazolyl,
e) a radical of the formula III, in which n is the number zero, 1, 2, 3 or 4, and m is the number zero or 1, Z is
1) —O—, or
2) —NH—, or $R^5$ and $R^6$ are, independently of each other,
1) a hydrogen atom,
2) $(C_1-C_2)$-alkyl,
3) phenyl, or
4) OH, or $R^6$ and $R^7$ are bonded to each other and together form a methylene group, or $R^7$ is
1) a hydrogen atom,
2) trifluoromethylsulfonyl,
3) an amino acid from the group Gly, Phe, Ala, Lys, Tyr or Ser, or
4) a radical of the formula IV, in which o is the number zero or 1, $R^9$ and $R^{10}$ are, independently of each other,
1) a hydrogen atom, or
2) methyl, $R^{11}$ is:
1) OH,
2) —O—$(C_1-C_4)$-alkyl,
3) $(C_1-C_{18})$-alkyl,
4) $(C_1-C_6)$-alkyl, substituted once or more than once, independently of each other, by
  4.1 —COOH,
  4.2 OH, or
  4.3 O-acetyl,
5) —COOH,

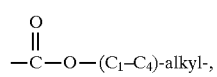

6)
7) N-glycyl,
8) N-glycyl-$(C_1-C_4)$-alkyl ester,
9) N-methylhydroxylamino,
10) N-(1H-tetrazol-5-ylamino),
11) 5-methylisoxazol-4-yl,
12) 1-cyano-2-hydroxy-1-propenyl, or 13) phenyl, substituted once by
  13.1) 4-(4-morpholino)methyl, f) a radical of the formula V, in which $Q_1$ is
1) —$(CH_2)_n$—, where m is the number zero, 1 or 2, or
2) —CH═CH—, and $R^8$ is
1) a hydrogen atom,
2) methyl,
3) OH,
4) —O—$(C_1-C_2)$-alkyl,
5) amino,
6) N-(1H-tetrazol-5-yl)amino, or
7) N-3,5-dimethyl-4-hydroxybenzyl, or g) a radical of the formula VI, in which $Q_2$ is
1) —$(CH_2)_m$—, where m is the number zero, 1 or 2, or
2) —CH═CH—, X and Y are, independently of each other,
1) methyl,
2) —O—$(C_1-C_2)$-alkyl, or
3) OH, ...A... is a double bond which is present or absent, with the restriction that the double bond and the radical $R^4$ are not present simultaneously, $R^4$ is
1) a hydrogen atom, or
2) $(C_1-C_2)$-alkyl, or $R^2$ and $R^4$ form, together with the carbon atom to which they are bonded, an aliphatic ring having 3, 4 or 5 carbon atoms, $R^3$ is
1) a hydrogen atom,
2) methyl, or
3) hydroxymethyl.

3. A compound of the formula I as claimed in claim 1 or 2, where one radical $R^1$ or $R^2$ has the meaning of the formula II and the other radical $R^1$ or $R^2$ has the following meaning:

a) 2-pyridyl,
b) 4-pyridyl,
c) thiophen-3-yl,
d) 2-thiazolyl,
e) a radical of the formula III, in which n is the number zero, 1, 2, 3 or 4, and m is the number zero or 1, Z is
1) —O—, or
2) —NH—, or $R^5$ and $R^6$ are, independently of each other,
1) a hydrogen atom,
2) $(C_1-C_2)$-alkyl, or
3) phenyl, or $R^6$ and $R^7$ are bonded to each other and are together a methylene group, or $R^7$ is
1) hydrogen,
2) trifluoromethylsulfonyl,
3) an amino acid from the group Gly, Lys or Phe, or
4) a radical of the formula IV, in which o is the number zero or 1, $R^9$ and $R^{10}$ are, independently of each other,
1) a hydrogen atom, or
2) methyl, $R^{11}$ is
1) OH,
2) O-methyl or O-ethyl,
3) $(C_1-C_{18})$-alkyl, 4) ($C_1$–$C_6$)-alkyl, substituted once or more than once, independently of each other, by
  4.1 —COOH,
  4.2 OH, or
  4.3 O-acetyl,
5) —COOH,
6)

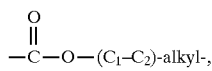

7) N-glycyl,
8) N-glycyl-($C_1$–$C_2$)-alkyl ester,
9) N-methylhydroxylamino,
10) N-(1H-tetrazol-5-ylamino),
11) 5-methylisoxazol-4-yl, or
12) 1-cyano-hydroxy-1-propenyl,
f) a radical of the formula V, in which $Q_1$ is
  1) —$(CH_2)_m$—, where m is the number 0, 1 or 2, or
  2) —CH=CH—, and
$R^8$ is
  1) a hydrogen atom,
  2) methyl,
  3) OH,
  4) —O—methyl,
  5) amino,
  6) N-(1H-tetrazol-5-yl)amino, or
  7) N-3,5-dimethyl-4-hydroxybenzyl, or
g) a radical of the formula VI, in which $Q_2$ is
  1) —$(CH_2)_m$—, where m is the number zero, or
  2) —CH=CH—,
X and Y are, independently of each other,
  1) methyl,
  2) —O—($C_1$–$C_2$)-alkyl, or
  3) OH,
...A... is a double bond which is present or absent, with the restriction that the double bond and the radical $R^4$ are not present simultaneously,
  $R^4$ is
    1) a hydrogen atom, or
    2) methyl, or
  $R^2$ and $R^4$ form, together with the carbon atom to which they are bonded, an aliphatic ring having 3, 4 or 5 carbon atoms,
  $R^3$ is
    1) a hydrogen atom, or
    2) hydroxymethyl.

4. A process for the preparation of 2-isoxazoline and isoxaole of the formula I, and/or a stereosomeric form of the compound of formula I, and/or a physiologically tolerated salt of the compound of the formula I, wherein a) a primary nitro compound is converted into the corresponding nitrile oxide using isocyanates and catalytic quantities of triethylamine, or a hydroxamoyl chloride, obtained by chlorinating a corresponding aldoxime, is converted into the corresponding nitrile oxide using an organic or inorganic base, and this nitrile oxide, obtained as an intermediate, is reacted, without purification, with an appropriately substituted olefin or alkyne, in the sense of a 1,3-dipolar cycloaddition, to form a 2-isoxazoline or isoxazole of the formula I, and the resulting product is, where appropriate, purified by crystallization or chromatography, or b) a carboxylic ester of the formula I, prepared in accordance with a) or o), or an ester group, additionally introduced via process h) or k), is hydrolyzed to the carboxylic acid, or c) an alkyl carboxylate of the formula I, prepared in accordance with process a) or o), is converted, using an appropriately substituted primary or secondary amine, into the corresponding amide, or d) a monoalkyl phosphinate or dialkyl phosphonate of the formula I, prepared in accordance with a) or o), is hydrolyzed to the phosphonic semi-ester, to the phosphonic acid or to the phosphinic acid, or e) a carboxylic acid, obtained in accordance with b), is initially converted into an activated acid derivative and this derivative is subsequently esterified with alcohols or converted, using primary and secondary amines, into the corresponding amide, or converted, using N-alkylated hyroxylamine, into the corresponding hydroxylamide, or f) N-protective group or O-protective group in a [lacuna] obtained or entrained as an intermediate in accordance with the processes a), b), h), e), o) or g) is eliminated, or carboxylic, phosphinic, phosphonic or phosphoric esters which are introduced or entrained are correspondingly hydrolyzed, and a compound of the formula I is obtained, or g) a compound obtained in accordance with processes f) or o), and having a free amino group, is converted into the corresponding urea derivative by reaction with isocyanate, or converted into the corresponding amide by reaction with an activated carboxylic acid derivative or an N-protected amino acid, or converted into the corresponding sulfonamide by reaction with a sulfonyl chloride, or h) a compound obtained in accordance with processes a), o) or f), and having a free alcohol group, is converted into the corresponding urethane by reaction with isocyanate, or converted into the corresponding ester by reaction with a carboxylic acid derivative which is activated at the carboxyl group and may carry further functional groups, or a corresponding N-protected amino acid derivative, or converted into the corresponding 3-oxobutyrate with diketene, or converted into the corresponding ether by reaction with a halogen compound such as α-halogen-carboxylic acid, or i) a compound obtained in accordance with processes a), o) or f), and having a primary or secondary alcohol group, is oxidized to the corresponding aldehyde or ketone, or k) a carbonyl compound prepared in accordance with process i) is converted into the corresponding crotonic acid derivative by reaction with a base and dialkylphosphonoacetic acid ester, or converted into the corresponding trans-2-(dialkoxyphosphono)vinyl derivative by reaction with tetraalkylmethylenediphosphonate, or l) an epoxide group introduced during the cycloaddition is converted into the corresponding 1,2-diol, or m) an amide prepared in accordance with process g), and containing a 3-H-isoxazole ring, is converted into the corresponding substituted 2-cyano-3-hydroxycrotonamide by treatment with a base in the sense of a ring opening, or n) a compound of the formula I prepared in accordance with processes a)–m), which compound, owing to its chemical structure, occurs in enantiomeric forms, is resolved into the pure enantiomers by salt formation with enantiomerically pure acids or bases, chromatography on chiral stationary phases, or derivatization using chiral enantiomerically pure compounds such as amino acids, separation of the diastereomers thus obtained, and elimination of the chiral auxiliary group, or o) a mixture of 2-isoxazoline diastereomers of the formula I, obtained by cycloaddition to chiral or racemic olefins, is resolved into the pure diastereomers by column chromatography on silica gel, or p) the compound of the formula I prepared in accordance with processes a)–o) is either isolated in free form or, where acid or basic groups are present, is, where appropriate, converted into physiologically tolerated salts, or q) a compound prepared in accordance with process h), which compound carries a further functional group such as a halomethyl group, is alkylated with a primary or secondary amino group or etherified with an alcohol.

5. A pharmaceutical composition containing an effective quantity of at least one compound of formula I as claimed in claim 1, and/or a physiologically tolerated salt of the compound of formula I and/or a stereoisomeric form of the compound of formula I, in addition to physiologically acceptable auxiliary substances and carrier substgances, and, where appropriate, further additives and/or other active compounds.

6. A pharmaceutical composition containing an effective quantity of at least one compound of formula I as claimed in claim 2, and/or a physiologically tolerated salt of the compound of formula I and/or a stereoisomeric form of the compound of formula I, in addition to physiologically acceptable auxiliary substances and carrier substgances, and, where appropriate, further additives and/or other active compounds.

7. A pharmaceutical composition containing an effective quantity of at least one compound of formula I as claimed in claim 3, and/or a physiologically tolerated salt of the compound of formula I and/or a stereoisomeric form of the compound of formula I, in addition to physiologically acceptable auxiliary substances and carrier substgances, and, where appropriate, further additives and/or other active compounds.

8. A pharmaceutical composition containing an effective quantity of at least one compound of formula I as obtained as claimed in claim 4, and/or a physiologically tolerated salt of the compound of formula I and/or a stereoisomeric form of the compound of formula I, in addition to physiologically acceptable auxiliary substances and carrier substgances, and, where appropriate, further additives and/or other active compounds.

9. The method of treating or preventing asthmatic diseases, inflammations and/or autoimmune diseases in a patient in need thereof comprising administering to the patient a therapeutically effective amount of a compound according to claim 1.

10. The method of treating or preventing asthmatic diseases, inflammations and/or autoimmune diseases in a patient in need thereof comprising administering to the patient a therapeutically effective amount of a compound according to claim 2.

11. The method of treating or preventing asthmatic diseases, inflammations and/or autoimmune diseases in a patient in need thereof comprising administering to the patient a therapeutically effective amount of a compound according to claim 3.

12. A process for preparing a pharmaceutical composition as claimed in claim 10, wherein at least one compound of formula I as claimed in claim 1 and/or a physiologically tolerated salt of the compound of the formula I and/or a stereoisomeric form of the compound of the formula I is brought into a suitable form for administration together with physiologically acceptable auxiliary substances and carrier substances and, where appropriate, further additives and/or other active compounds.

* * * * *

UNITED STATES PATENT AND TRADEMARK OFFICE
CERTIFICATE OF CORRECTION

PATENT NO. : 5,814,627
DATED : September 29, 1998
INVENTOR(S) : Wilfried Schwab et al.

It is certified that error appears in the above-identified patent and that said Letters Patent is hereby corrected as shown below:

Title Page, Item [73], in the Assignee, line 1, "Aktienegesellschaft" should read --Aktiengesellschaft--.

Title Page, Item [57], in the Abstract, line 3, "steroisomeric" should read --stereoisomeric--.

Claim 1, col. 68, lines 38-40, in the formula (V),

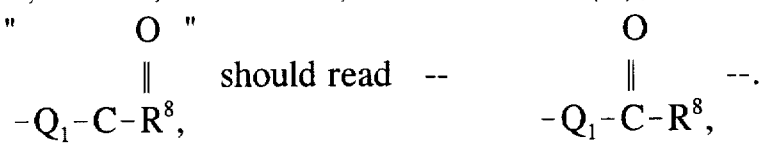

On the line after "5) -COOH," in Claim 2, col. 69, line 55, insert --6)--; and in Claim 2, col. 69, line 61, delete "6)".

Claim 2, col. 70, line 27, "$(C_l-C_2)$-alkyl" should read --$(C_1-C_2)$-alkyl--.

Claim 4, col. 71, line 51, "isoxaole" should read --isoxazole--; and "stereosomeric" should read --stereoisomeric--.

Claim 4, col. 72, line 17, "hyroxylamine" should read --hydroxylamine--.

Claim 4, col. 72, line 19, delete "in a [lacuna]".

Claim 5, col. 73, line 25, "substgances" should read --substances--.

Claim 6, col. 73, line 33, "substgances" should read --substances--.

Claim 7, col. 74, line 3, "substgances" should read --substances--.

Claim 8, col. 74, line 11, "substgances" should read --substances--.

UNITED STATES PATENT AND TRADEMARK OFFICE
CERTIFICATE OF CORRECTION

PATENT NO. : 5,814,627
DATED : Sept. 29, 1998
INVENTOR(S) : Wilfried Schwab et al.

It is certified that error appears in the above-identified patent and that said Letters Patent is hereby corrected as shown below:

Claim 12, col. 74, line 30, "claim 10" should read --claim 7--.

Signed and Sealed this

Twenty-first Day of March, 2000

Attest:

Q. TODD DICKINSON

Attesting Officer         Commissioner of Patents and Trademarks